United States Patent [19]
Montgomery et al.

[11] Patent Number: 6,001,840
[45] Date of Patent: Dec. 14, 1999

[54] METHODS OF TREATMENT OF VIRAL INFECTIONS USING CARBOCYCLIC DEOXYGUANOSINE ANALOGS

[75] Inventors: John A. Montgomery; John A. Secrist, III; L. Lee Bennett; William B. Parker; Y. Fumer Shealy, all of Birmingham, Ala.; David I. Scheer, Guilford, Conn.

[73] Assignee: Southern Research Institute, Birmingham, Ala.

[21] Appl. No.: 08/020,220

[22] Filed: Feb. 19, 1993

Related U.S. Application Data

[63] Continuation-in-part of application No. 07/776,895, Oct. 16, 1991, which is a continuation of application No. 07/489,458, Mar. 6, 1990, abandoned.

[51] Int. Cl.[6] .................................................... A61K 31/52
[52] U.S. Cl. ......................... 514/261; 514/262; 544/276; 544/277
[58] Field of Search ..................... 514/261, 262

[56] References Cited

U.S. PATENT DOCUMENTS

| 4,177,348 | 12/1979 | Shealy et al. | 544/317 |
|---|---|---|---|
| 4,232,154 | 11/1980 | Shealy et al. | 544/250 |
| 4,396,623 | 8/1983 | Shealy et al. | 424/251 |
| 4,543,255 | 9/1985 | Sheely et al. | 514/258 |
| 4,728,736 | 3/1988 | Shealy et al. | 544/254 |
| 4,857,531 | 8/1989 | Borthwick et al. | 514/262 |
| 4,916,224 | 4/1990 | Vince et al. | 544/254 |
| 4,931,559 | 6/1990 | Vince et al. | 544/276 |
| 4,950,758 | 8/1990 | Vince et al. | 544/276 |

FOREIGN PATENT DOCUMENTS

| 219 838 | 4/1987 | European Pat. Off. . |
|---|---|---|
| 0 236 935 | 9/1987 | European Pat. Off. . |
| 236 935 | 9/1987 | European Pat. Off. . |
| 0 322 854 | 7/1989 | European Pat. Off. . |
| 0 352 248 | 1/1990 | European Pat. Off. . |
| 233 146 | 3/1989 | Japan . |
| WO 88/04662 | 6/1988 | WIPO . |

OTHER PUBLICATIONS

Bennett, Jr. et al., Annals NY Acad Sci. 255:342–358, 1975, "Studies on the Biochemical Basis for the Antiviral Activities of Some Nucleoside Analogs."
Bavand et al., Journal of Virology 63:1019–1021, 1989, "The Hepatitis B Virus–Associated Reverse Transcriptase Is Encoded by the Viral pol Gene."
Beach et al., Journal of Org. Chem. 57:2217–2219, 1992, "Syntheses of Enantiomerically Pure (2'R, 5'S)–(–)–1–[2–(Hydroxymethyl)oxathiolan–5–yl]cytosine as a Potent Antiviral Agent against Hepatitis B Virus . . . ".
Buthala, Annals NY Acad Sci. pp. 17–22, 1991, "Experience Gained in Screening for Synthetic Antiviral Compounds."
Bosch et al., in RNA Genetics vol. II, Domingo et al. (eds) CRC Press pp. 43–58, 1988, Hepatitis B Virus Replication.
Dahlberg et al., Proc. Natl. Acad. Sci. USA 84:2469–2473, 1987, "Broad Spectrum Antiretroviral Activity of of 2',3'–Dideoxynucleosides."
Furman et al., Antimicrobial Agents and Chemotherapy 36:2686–2692, 1992, "The Anti–Hepatitis B Virus Activities, Cytotoxicities, and Anabolic Profiles of the (–) and (+) Enantiomers of . . . Cystosine."
Gerin, Hematology 14:198–199, 1991, "Antiviral Agents for Hepatitis B."
Hoofnagle et al., "Antiviral Therapy of Viral Hepatitis," In Antiviral Agents and Viral Diseases of Man, Galasso et al., (eds.), Raven Press, Ltd., New York, NY, Chapter 12, pp. 415–459, 1990.
Kassianides et al., Gastroenterology 94:A552, "Effect of 2',3'–Dideoxycytidine on Duck Hepatitis B Virus", 1988.
Korba et al., Antiviral Research, 19:55–70, 1992, "Use of a standardized cell culture assay to assess activities of Nucleoside Analogs Against Hepatitis B Virus Replication."
Korba et al., Antiviral Research, 15:217–228, 1991, "A Cell Culture Assay for Compounds Which Inhibit Hepatitis B Virus Replication."
Lee et al., Antimicrobial Agents and Chemotherapy, 33:336–339, 1989, "In Vitro and In Vivo Comparison of of the Abilities of Purine and Pyrimidine 2',3'–Dideoxynucleosides To Inhibit Duck Hepadnavirus."
Nordenfelt et al., Journal of Medical Virology 22:231–236, 1987, "Inhibition of Hepatitis B Virus DNA Polymerase by 3'–Azido–3'–Deoxythymidine Triphosphate but not by Its Threo Analog."
Ponzetto et al., Hematology 14:16–24, 1991, "Adenine Arabinoside Monophosphate and Aclyclovir Monophosphate Coupled to Lactosaminated Albumin Reduce Woodchuck Hepatitis Virus Viremia at Doses Lower Than . . . ".
Price et al., Proceedings of the National Academy of Science U.S.A., 86:8541–8544, 1989, "Inhibition of Replication of Hepatitis B Virus by the Carbocyclic Analogue of 2'–Deoxyguanosine."
Price et al., Pharmacology 117:142894c, 1992, "The Mechanism of Inhibition of Hepatitis B Virus Replication by the Carbocyclic Analog of 2'–Deoxyguanosine."
Schiff, The American Journal of Gastroenterology 82:287–291, 1987, "Immunoprophylaxis of Viral Hepatitis: A Practical Guide."
Secrist et al., Journal of Medicinal Chemistry, 30:746–749, 1987, "Resolution of Racemic Carbocyclic Analogues of Purine Nucleosides through the Action of Adenosine Deaminase. Antiviral Activity of the . . . ".
Shannon, Annals NY Academy, Sci. 284:472–507, 1977, "Selective Inhibition of RNA Tumor Virus Replication In Vitro and Evaluation of Candidate Antiviral Agents In Vivo."
Shealy et al., J. Med. Chem. 30:1090–1094, 1987, "Synthesis and Antiviral Evaluation of Carbocyclic Analogues of 2–Amino–6–substituted–purine 3'–Deoxyribofuranosides."

(List continued on next page.)

Primary Examiner—Richard L. Raymond
Attorney, Agent, or Firm—Fish & Richardson P.C.

[57] ABSTRACT

Method for prophylaxis and treatment of a viral infection characterized by the administration of a composition comprising a substantial molar excess of the D-stereoisomer of 2'CdG over the L-stereoisomer.

8 Claims, 9 Drawing Sheets

OTHER PUBLICATIONS

Summers et al., Cell 29:403–415, 1982, "Replication of the Genome of a Hepatitis B–Like Virus by Reverse Transcription of an RNA Intermediate."

Suzuki et al., Biochem. Biophys. Res. Comm. 156:1144–1151, 1988, "Inhibition of Duck Hepatitis B Virus Replication by Purine 2',3'–Dideoxynucleosides."

Tabor, Viral Hepatitis and Liver Disease, A.J. Zuckerman (ed.), A.R.Lis, Inc. NY, 902–905, 1988, "Experimental Drugs for the Treatment of Viral Hepatitis: Drugs That Interfere With Viral Replication."

Thomas, Viral Hepatitis and Liver Disease, A.J. Zuckerman (ed.), A.R.Lis, Inc. NY, 817–822, 1988, Treatment of Hepatitis B Viral Infection.

Toh et al., Nature 305:827–829, 1983, "Sequence Homology Between Retroviral Reverse Transcriptase and Putative Polymerases of Hepatitis B Virus and Cauliflower Mosaic Virus."

Trépo et al., Journal of Hematology, 3:S129–S135, 1986, "Therapeutic Potential of Acyclovir and of the Interferons in HBV–Related Chronic Active Hepatitis due to HBV With or Without HDV Superinfection."

Ueda et al., Virology 169:213–216, 1989, "Short Communications—An In Vitro System for Screening Anti–Hepatitis B Virus Drugs."

Will et al., Journal of Virology 61:904–911, 1987, "Replication Strategy of Human Hepatitis B Virus."

Zuckerman, Journal of Virological Methods 17:119–126, 1987, "Screening of Antiviral Drugs for Hepadna Virus Infection in Pekin ducks: A Review."

Rosecan et al., Am. J. Opthalmol., 101:405–418, 1986, "Antiviral Therapy for Cytomegalovirus Retinitis in Aids with DihydroxyPropoxymethyl."

De Clercq et al., Antiviral Research, 3:17–24, 1983, "Broad Spectrum Antiviral Activity of the Carbocyclic Analog of 3–Deazaadenosine."

Shealy et al., Journal of Medicinal Chemistry, 27:670–674, 1984, "Synthesis & Antiviral Evaluation of Carbocyclic Analogues of Ribofuranosides of 2–Amino–6–Substituted–purines and 2–Amino–6–Substituted . . . ".

Field, (ed.) In Antiviral Agents: The Development and Assessment of Antiviral Chemotherapy, p. 10, CRC Press, Inc. Boca Raton, Florida, 1988.

Fields et al., (eds.), Virology, Raven Press, New York, pp. 498, 499, 503, 508, 580, 630, 650, 651, 1985.

Boyd et al., Antimicrobial Agents and Chemotherapy, 31:1238–1242, 1987, "Antiherpesvirus Activity of 9–(4–Hydroxy–3–Hydroxymethylbut–1–yl)Guanine (BRL 39123) in Cell Culture."

Buthala et al., Annals NY Acad Sci. 130:17–23, 1965, Experience Gained in Screening for Synthetic Antiviral Compounds.

Machida, Antimicrob. Agents and Chemotherapy, 29:524–526, 1986, "Comparison of Susceptibilities of Varicella–Zoster Virus and Herpes Simplex Viruses to Nucleoside Analogs."

DeClercq, Verh. K. Acad., Geneeskd. Belg. 50:261–290. 1988, "Towards a Selective Chemotherapy of Virus Infections. Development of Bromovinyldeoxyuridine. . . ".

Biggadike et al., J. Chem. Soc. Commun., 1083–1084, 1987, "Short Convergent Route to Homochiral Carbocyclic 2'–Deoxynucleosides and Carbocyclic Ribonucleosides."

Shealy et al., J. Pharm. Sci., 62:1432–1434, 1973, "Carbocyclic Analogs of Guanosine and 8–Azaguanosine."

Shealy et al., J of Med. Chem., 27:1416–1421, 1984, "Synthesis and Antiviral Activity of Carbocyclic Analogues of 2'–Deoxyribofuranosides of 2–Amino–6–substituted–purines and of 2–Amino–6–substituted–8–. . . ".

De Clercq et al., Antiviral Research 4:119–133, 1984, "Broad–spectrum antiviral activity of adenosine analogues."

Vince et al., Antiviral Research, 9:120, 1988, "Second International Conference on Antiviral Research, Williamsburg, VA, 1988."

Shealy et al., J of Heterocyclic Chem., 13:1015–1020, 1976, "Synthesis of the Carbocyclic Analogs of Uracil Nucleosides."

Shealy et al., J of Heterocyclic Chem., 13:1041–47, 1976, "Acid Catalyzed Cyclization of Alkoxyacryloylureas to 2.4 (1H, 3H) pyrimidinediones."

Shealy et al., J of Med. Chem., 26:155–165, 1983, "Carbocyclic Analogues of S–Substituted Uracil Nucleoside: Synthesis and Antiviral Activity."

Shealy et al., Journal of Heterocyclic Chem., 13:1353–1354, 1976, "The Carbocyclic Analog of Cytidine, Synthesis and Anti–neoplastic Activity."

Shealy et al., Journal of Heterocyclic Chem., 17:353–358, 1980, "Carbocyclic Analogs of Cytosine Nucleosides."

Shealy et al., Journal of Heterocyclic Chem., 18:383–89, 1981, "Carbocyclic Analogs of Thymines Nucleosides & Related I–Substituted Thymines."

Balzarini et al., Molecular Pharmacology 37:395–401, 1989, "Carbocyclic 5–lodo–2'–deoxyuridine (C–IDU) and Carbocyclic (E)–5–(2–Bromovinyl)–2'–deoxyuridine . . . Thymidine Kinase of Herpes Simplex Virus Type 1."

Bennett et al., Biochemical Pharmacology 40:1515–1522, 1990, "Phosphorylation of the Carbocyclic Analog of 2'–Deoxyguanosine in Cells infected with Herpes Viruses."

Biron et al., Proc. Natl. Acad. Sci. USA 83:8769–8773, 1986, "A human cytomegalovirus mutant resistant to the nucleoside analog 9–{[2–hydroxy–1–(hydroxymethyl)ethoxy]methyl} . . . levels of BW B759U triphosphate."

Brigden et al., J. of Antimicrobial Chemotherapy 12:195–199, 1983, "The present and future for acyclovir."

Chu et al., J. Org. Chem., 56:6503–6505, 1991, "Enantiomeric Synthesis of (+)–BCH–189 [(+)–(2S,5R)–1–[2–(Hydroxymethyl)–1,3–oxathiolan–5–yl]cytosine] from D–Mannose and Its Anti–HIV Activity."

Coates et al., Antimicrobial Agents and Chemotherapy 36:202–205, 1992, "The Separated Enantiomers of 2'Deoxy–3' Thiacytidine (BCH 189) Both Inhibit Human Immunodeficiency Virus Replication In Vitro."

Collins, J.of Antimic. Chemtrpy. 12:19–27, 1983, "The Spectrum of Antiviral Activities of Acyclovir in vitro and in vivo."

Dong et al., Carcinogenesis 12:1125–1128, 1991, "Hydrolysis of Carcinogen–DNA adducts by three classes of Deoxyribonucleosidase to their Corresponding Bases."

Elion, Antimicrobial Chemotherapy 12:9–17, 1983, "The Biochemistry and Mechanism of Action of Acyclovir."

M.G. Falcon, J. of Antimicrobial Chemotherapy 12:39–43, 1983, "Herpes Simplex Virus Infections of the Eye and Their Management with Acyclovir."

Meyers et al., J. of Antimicrobial Chemotherapy 12:181–193, 1983, "The use of acyclovir for cytomegalovirus infections in the immunocompromised host."

Parker et al., Antiviral Research 19:325–332, 1992, "Interference with HIV–1 reverse transcriptasecatalyzed DNA chain elongation by the 5'–triphosphate of the carbocyclic analog of 2'–deoxyguanosine."

Parker et al., Molecular Pharmacology 41:245–251, 1991, "Incorporation of the Carbocyclic Analog of 2'–Deoxyguanosine into the DNA of Herpes Simplex Virus and of HEp–2 Cells Infected with Herpes Simplex Virus."

H. Prentice, J. of Antimicrobial Chemotherapy 12:153–159, 1983, "Use of acyclovir for phophylaxis of herpes infections in severely immunocompromised patients."

Schinazi et al., Antimicrobial Agents and Chemotherapy 36:2423–2431, 1992, "Selective Inhibition of Human Immunodeficiency Viruses by Racemates and Enantiomers . . . Cytosine."

Spadari et al., J. Med. Chem. 35:4214–4220. 1992, "L–Thymidine Is Phosphorylated by Herpes Simplex Virus Type 1 Thymidine Kinase and Inhibits Viral Growth."

Taniyama et al., Nucleosides & Nucleotides 11:529–549, 1992, "Carbocyclic Purine Nucleosides Derived From Aristeromycin Through Two Key Intermediates . . . Riboside and 2'–Deoxyriboside."

METHODS OF TREATMENT OF VIRAL INFECTIONS USING CARBOCYCLIC DEOXYGUANOSINE ANALOGS

This application is a continuation-in-part of U.S. Ser. No. 07/716,895, filed Oct. 16, 1991, which was a continuation of U.S. Ser. No. 07/489,458, filed Mar. 6, 1990, now abandoned.

BACKGROUND OF THE INVENTION

This invention relates to the use of the carbocyclic analogue of 2'-deoxyguanosine (2'CdG) in the prophylaxis and treatment of infections by viruses including herpes simplex virus types I and II, cytomegalovirus, and hepatitis B virus.

Among the many kinds of viruses that infect man, two types are especially important with regard to their ubiquity, clinical significance and economic impact: the herpes viruses and the hepatitis viruses.

The six human herpesviruses, herpes simplex virus types 1 and 2 (HSV-1, HSV-2), varicella-zoster virus (VZV), cytomegalovirus (CMV), Epstein-Barr virus (EBV), and human herpes virus 6 (HHV 6), are widely disseminated in the population and are responsible for a broad spectrum of human diseases, ranging from minor annoyances such as cold sores to highly destructive infections of the central nervous system (encephalitis), and potentially fatal neonatal infections. Once infected, an individual may suffer lesions and recover, but the virus usually persists for the life of the individual in a state of latency in nerve or other cells and may periodically become reactivated to cause recurrent clinical lesions or other disease states. In addition, it has been long recognized that herpesvirus infections are considerably more severe in certain immunosuppressed patients, particularly those with depressed cell-mediated immunity such as cancer patients and organ transplant recipients, individuals with hereditary immune deficiencies, as well as individuals with acquired immune deficiency syndrome (AIDS).

HSV-1 and HSV-2 manifest themselves in a number of clinical diseases, including infections of the central nervous system (encephalitis), skin, lips, and the genitalia. Oral herpes is caused generally by HSV-1 and genital herpes by HSV-2, but both viruses can cause either infection (and each can cause encephalitis). The estimated annual number of episodes of recurrent herpes labialis is over 100 million in the United States alone. It also has been estimated that over 1,000,000 new clinically reported cases of genital herpes occur each year in the United States, and that currently as many as 60 million cases per year of recurrent genital herpes may exist. In addition, a large number of individuals will excrete virus in the absence of clinical symptoms and thus constitute a silent but persistent reservoir for transmission of virus through sexual contacts.

Human cytomegalovirus (CMV) infections are among the most common cause of congenital (human intrauterine and perinatal) infection in the world today, and represent a frequent and serious complication in immunosupressed inividuals. Congential CMV infections are associated with retinitis, hearing loss, birth defects, mental retardation, and death. In immunosuppressed adults, CMV is associated with serious infections of the eye such as chorioretinitis, as well as infections of other organs, including hepatitis, esophagitis, gastritis, pneumonitis and encephalitis.

Hepatitis B virus (HBV) is the most prevalent of the highly contagious hepatitis viruses, infecting an estimated 200 million people worldwide. HBV is a major cause of acute and chronic hepatitis, cirrhosis, and primary hepatocellular carcinoma. Of the estimated 200,000–250,000 people in the United States who are infected annually, more than 100,000 require hospitalization and approximately 250 die of active disease each year. Between 6% and 10% of infected individuals become carriers of the virus. Approximately 25% of these carriers will develop cirrhosis and approximately 1% will develop hepatocellular carcinoma.

Other than exclusion of virus-host contact, there are two types of defenses against viral infection: vaccination and chemotherapy. Vaccination has had some success in preventing or limiting certain viral infections. However, there are certain limitations associated with the use of vaccines. First, vaccination, with rare exception, is a prophylactic measure which is useful only prior to the onset of the disease. Second, factors such as the age of the individual, the presence of preexisting antibody, either passively acquired maternal antibody or antibody secondary to natural infection, and the site of injection may influence the effectiveness of some vaccines. In addition, vaccination involves the introduction into the body of material which can, in some instances, pose risks which result in adverse reactions in the individual.

A number of nucleoside analogs have been proposed for chemotherapeutic treatment of viruses such as HSV, HBV and CMV. U.S. Pat. No. 4,396,623 (Shealy et al.) refers to the use of certain carbocyclic analogs or uracil nucleosides for the treatment of various human and animal diseases caused by DNA viruses, such as Herpes simplex virus. U.S. Pat. No. 4,177,348 (Shealy et al.) and U.S. Pat. No. 4,232,154 (Shealy et al.) refer to carbocyclic analogues of cytosine nucleosides and their activity against DNA viruses, such as herpes simplex virus Type 1. U.S. Pat. No. 4,543,255 (Shealy et al.) and U.S. Pat. No. 4,728,736 (Shealy et al.) refer to carbocyclic analogues of purine 2'-deoxyribofuranosides and ribofuranosides, respectively, and their activity against DNA viruses, exemplified by herpes simplex virus Type 1 and Type 2.

Of the nucleoside analogs available, acyclovir (acyloguanosine) is the agent currently indicated for the topical, oral or intravenous therapy of a number of clinical manifestations of HSV-1 and HSV-2 as it is a potent inhibitor of HSV replication. However, a number of toxic effects have been reported. Topical application of acyclovir can cause transient stinging, keratitis, follicular conjunctivitis and allergies when used to treat herpetic keratitis. Infusion may produce nephrotoxicity in patients receiving large doses due to deposition of drug crystals in renal tubules. Other toxic effects have been attributed to the high pH (alkalinity) required to keep acyclovir in solution. Furthermore, while the antiviral activity of acyclovir has been ascribed to its ability to be incorporated into the viral DNA, acyclovir induced-DNA chain incorporation and termination of cellular genes may lead to additional forms of toxicity, including chromosomal damage.

Acyclovir has also been used against HBV although its use is disadvantaged by the same potential side effects described above. In addition, while it is effective during short term administration in reducing markers associated with HBV replication, such as plasma levels of HBV DNA polymerase, cessation of drug administration may result in the return to pretreatment level of virus replication.

Other drugs currently used to treat HBV include adenosine arabinoside (ara-A) and adenine arabinoside monophosphate (ara-AMP, a form of the drug which allows it to be administered intramuscularly). These drugs are effective alone or in combination in decreasing levels of circulating HBV DNA polymerase activity in patients infected with HBV. However, complete inhibition of HBV may not result from these treatments, as DNA polymerase activity has been demonstrated to increase following cessation of drug therapy. Furthermore, both ara-A and ara-AMP are also associated with substantial toxicity. Untoward effects of these drugs commonly experienced by patients include nausea, anorexia, fatigue, diarrhea, vomiting, and reversible bone marrow suppression with thrombocytopenia. In addition, a peculiar neuromuscular pain syndrome that produces pain and cramping, most pronounced at the site of injection, and which may last for months following cessation of drug administration has been described. Payne, John A. "Chronic Hepatitis: Pathogenesis and Treatment," *Disease a Month*, March, pp. 117–59 (1988).

Acyclovir has also been used for prophylaxis of CMV, but has been reported to be ineffective against established systemic CMV infections as well as against CMV retinitis. Broad spectrum antibiotics, corticosteroids, and antifungal agents have also been reported to be without therapeutic benefit against this disease. An antiviral agent, ganciclovir (dihydroxy propoxymethyl guanine) (DHPG) an acyclic nucleoside, has been reported to be effective against CMV retinitis but is of limited potency and is associated with dose-limiting toxicity. Its activity is described in Declercq et al., *Antiviral Research* Vol. 3, 17–24 (1983) and Vol. 4, 119–133 (1984).

The carbocyclic analogue of 2'-deoxyguanosine(±)-2-amino-1,9-dihydro-[(1α,3β,4α)-3-hydroxy-4 (hydroxymethyl)cyclopentyl]-6H-purin-6-one] (2'-CdG) has been reported to have in vitro antiviral activity against HSV-1 and HSV-2 (Shealy et al., *J. Med. Chem.* 27:1416, 1987), human cytomegalovirus (Shannon et al., in Advances in Chemotherapy of AIDS, Diasio et al., eds., Pergamon Press, Inc., New York pp.75–95, 1990, as well as CMV (WO91/13549, 1991)), and human hepatitis-B virus (Price et al., Proc. Natl. Acad. Sci. USA 86:8541, 1989). In addition, it has also shown in vivo antiviral activity against HSV-1 and HSV-2 (Shannon et al., in *Proceedings of the American Society of Virology*, Annual Meeting, 1985).

SUMMARY OF THE INVENTION

We have found that the balance of antiviral efficacy and toxicity risk associated with using 2'CdG antiviral agents is substantially improved by using the D-isomer of such agents. Accordingly, the invention features a method for preventing or treating a viral infection in a mammal characterized by administering an antiviral effective amount of a composition comprising a compound of the formula

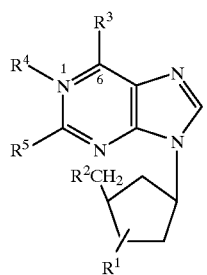

wherein, the composition comprises a substantial molar excess of the D-stereoisomer of the compound over the L-stereoisomer of the compound; $R^1$ is selected from the group consisting of, hydroxyl, and $C_1$–$C_6$ acyloxy; $R^2$ is selected from the group consisting of hydroxyl, and $C_1$–$C_6$ acyloxy; and $R^3$ is oxygen bound through a double bond to carbon when $R^4$ is hydrogen, or $R^3$ is chosen from the group consisting of $C_1$–$C_6$ alkoxy, amino, and halogen when $R^4$ is bound to carbon 6 to form a double bond between the nitrogen of position 1 and the carbon of position 6 and $R^5$ is amino.

By "substantial molar excess" as used herein is meant that more than 70%, more preferably 80%, even more preferably 90%, and most preferably more that 95% of the compound in the composition is in the form of the D-isomer. By D-enantiomer is meant the enantiomer corresponding in configuration to DGuo.

The term "carbocyclic analogue" as used herein refers to compounds which possess a cyclopentane ring in place of the tetrahydrofuran ring of the nucleoside compound.

In preferred embodiments, the composition contains the compound 2'CdG. Also greatly preferred are the prodrugs of 2'CdG, that is, those compounds that are metabolized in vivo to 2'CdG. Examples of prodrugs would include, but not be limited to, such compounds as various O-acylated esters, the 5'-O-phosphate, D-2'CdG analogues with a substituent at C-6 that is metabolized to D-2'CdG, and substituents such as alkoxy, halogen, methylthio, hydrogen, amino, or methylamino.

The method of the invention is especially effective in the prevention and treatment of herpesviruses including HSV-1, HSV-2 and cytomegalovirus, as well as hepatitis viruses such as hepatitis B virus.

Depending on the route of administration, which could normally be intravitreal injection (e.g., in treatment of cytomegalovirus induced chorioretinitis), topical, oral, intravenous or parenteral, compositions may be in the form of a solute, solid, semi-solid, liquid, oil, ingestible capsule or liposome or microencapsulated dosage form. In addition, the compounds may be present as the original compound or in the form of a pharmaceutically acceptable salt, and the compostion may include a pharmaceutically acceptable non-toxic carrier.

DETAILED DESCRIPTION

Drawings

The drawings will first be briefly described.

Figure 8:
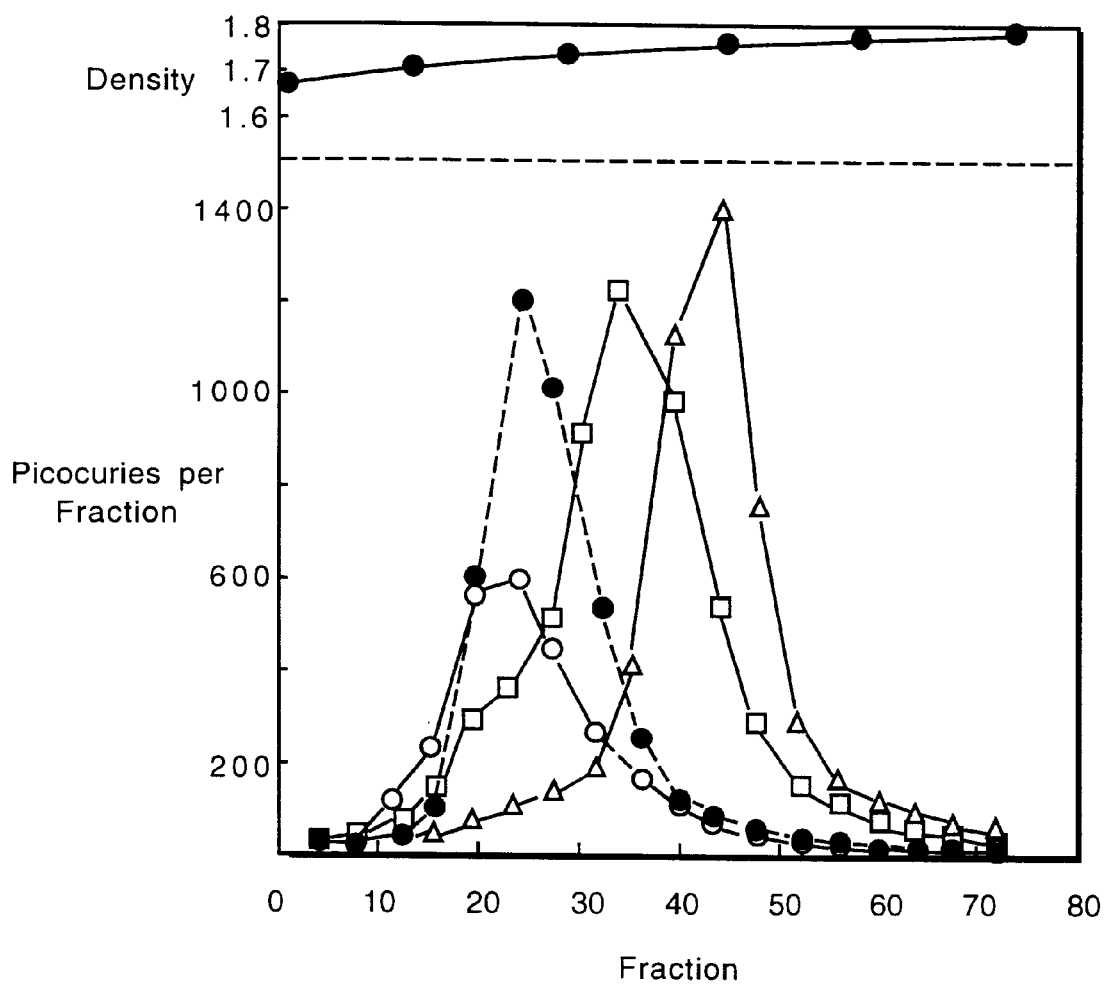

FIG. 8 is a graph illustrating the incorporation of [3H]-D-2'CdG into viral and cellular DNA. HSV-1-infected H.Ep.-2 cells were incubated with 8 µM [$^3$H]-D-2'CdG for 9 hr starting at the time of infection (○), with 1 µM [$^3$H]-D-2'CdG for 5 hr starting 4 hr after infection (Δ), or with 8 µM [$^3$H]-D-Cdg for 5 hr starting 4 hr after infection (□). $^{14}$C-labeled host DNA (•, dashed line).

Figure 9A:
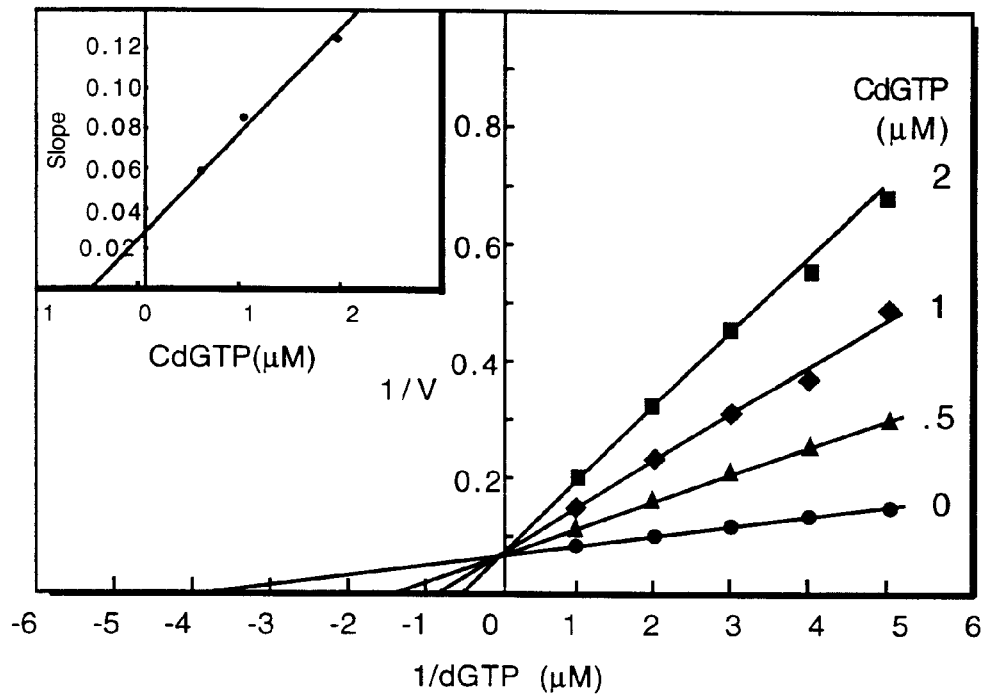
Figure 9B:
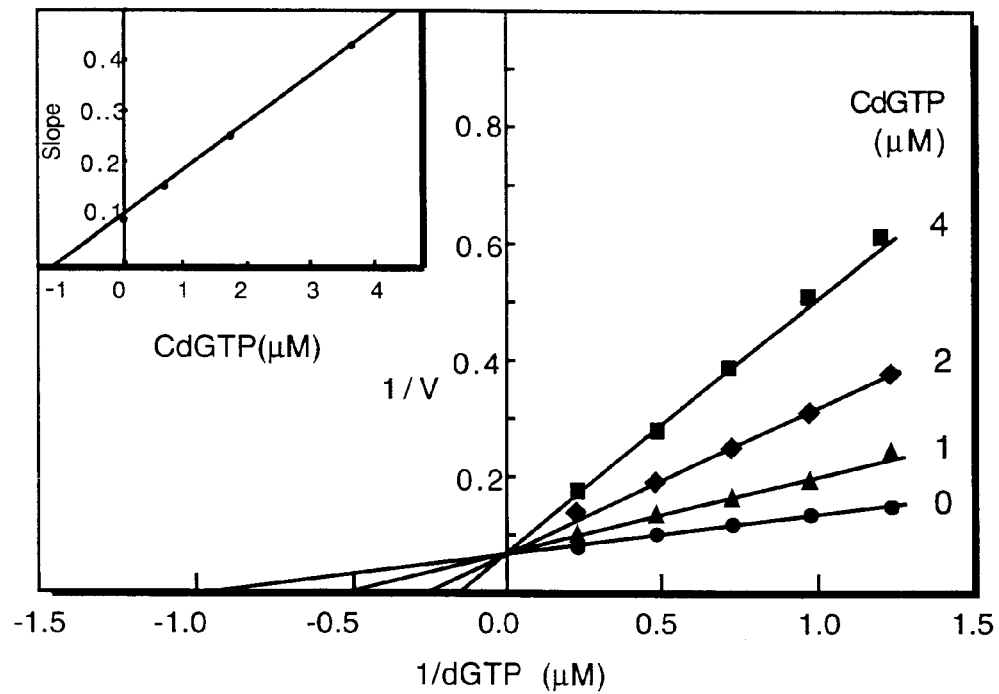

FIG. 9 depicts lineweaver-Burk and Dixon plots of the competitive inhibition of HSV DNA polymerase and host DNA polymerase a by [$^3$H]dGTP.

CHEMICAL SYNTHETIC SCHEME

The enantiomers of 2'CdG and related compounds according to this invention may be prepared using the appropriate optically active starting materials. For example, the D and L forms may be prepared by an enzymatic method as described by Secrist et al. (*J. Med. Chem.* 30:746, 1987). Generally, in this method the racemic carbocyclic analogue of 2,6-diaminopurine 2'deoxyribofuranoside (C-2,6-DAPR) is subjected to the action of commercially available adenosine deaminase for a short period at low concentration to yield D-2'-CdG and C-2,6-DAPdR. Then the unconverted C-L-2,6-DAPdR isolated from the filtrate may be converted to L-2'-CdG by increasing the concentration of adenosine deaminase, raising the temperature, and lengthening the reaction time.

Alternatively, synthesis can involve schemes which use optically inactive starting materials and which introduce optical activity at later steps, using enzymes which operate preferentially on one stereoisomer such as Pseudomonas fluorescens lipase, pig lever esterase, pig pancreatic lipase, Mucoimieties lipase, or 5' nucleotidase from *Crotalus atrax* venom. After that reaction, chemical separations of starting materials from products will provide optically active fragments.

A detailed description of one preferred method of preparing the enantiomers of 2'CdG is given below.

General Methods

Melting temperatures (mp) were determined in capillary tubes heated in a Mel-Temp apparatus. Ultraviolet spectra (UV) were recorded with a Cary Model 17 spectrophotometer, and absorption maxima are reported in nanometers: sh=shoulder. Solutions for ultraviolet determinations were prepared by diluting a 5-mL aliquot of a water solution of the carbocyclic analogue to 50 mL with 0.1 N hydrochloric acid, phosphate buffer (pH 7), or 0.1 N sodium hydroxide. Absorption maxima of these solutions are reported as being determined at pH 1,7, or 13, respectively. Extinction coefficients are given in parentheses. Mass spectra were determined at 70 eV by the fast-atom-bombardment (FAB) method and with a Varian/MAT 311A spectrometer. Elemental analyses were performed by Atlantic Microlab., Inc., Atlanta, GA, and the Molecular Spectroscopy Section of Southern Research Institute. Thin-layer chromatography (TLC) was performed on plates of silica gel, and developed plates were examined with ultraviolet light. High-pressure liquid chromatography (HPLC) was performed with a Hewlett-Packard 1084B liquid chromatograph equipped with a variable-wavelength detector set at 280 nm, an automatic injector, and a $C_{18}$ µ-Bondapak ODS 10-µm column. Isolated specimens were dissolved in water at a concentration of 1 mg/mL. In order to determine accurately the progress of the deamination reactions with an ultraviolet detector, standards of racemic starting materials and products were run in order to calibrate peak areas. Unless indicated otherwise, aliquots of reaction solutions and most isolated specimens were assayed by using a gradient eluting solvent of water-acetonitrile (9:1--1:9 over 20 min); flow rate, 1 mL/min. Some of the aliquots and the analytical samples of D-2'-CdG, L-2'-CdG, and C-L-2,6-DAP-2'-dR were also assayed by using a gradient eluting solvent of 0.01 M $NH_4H_2PO_4$ (pH 5.1)-MeOH (9:1--1:9 over 20 min). Optical rotations were measured with a Perkin-Elmer Model 141 polarimeter. Yield calculations are based upon conversion of one-half of the racemic starting materials.

[1R,2S,3R,4R-(1α,2β,3β,4α)]-D-1,9-Dihydro-9-[2,3-dihydroxy-4-(hydroxymethyl)cyclopentyl]-6H-purin-6-one (D-C-Ino, 4a) and [1S,2R,3S,4S-(1α,2β,3β,4α)]-L-4-(6-Amino-9H-purin-9-yl)-2,3-dihydroxycyclopentanemethanol(L-C-Ado).

A solution of 400 mg (1.51 mmol) of carbocyclic adenosine in 80 mL of hot water was cooled to room temperature before the addition of 100 µL (250 units) of Adenosine aminohydrolase (EC 3,5,4,4) (ADA from calf intestinal mucosa, purchased from Sigma Chemical Co., St. Louis, Mo. 63178; Product No. A-1030, Type VIII). After being stirred for 3 h at room temperature, the solution was boiled for 5 min., filtered through Celite, and examined by TLC and HPLC, which shows 52.3% carbocyclic inosine (0.79 mmol., 210 mg), leaving 0.72 mmol, 200 mg of carbocyclic adenosine. The solution was applied to an ion-exchange column (diameter 1 cm) containing 3.3 mL (3 equiv) of Amberlite IRA 400(OH$^-$). The column was then eluted with 500 mL of water to remove the adsorbed C-Ado (no further C-Ado was observed by TLC). Evaporation of this solution to dryness followed by recrystallization from water gave 143 mg (71.5%) of L-C-Ado: $[α]^{23}$p+51.1° (c 0.3, DMF); mp 208–210° C. (racemic C-Ado, 244 C°); HPLC 98.67%; TLC, homogeneous in (3:1 CHCl$_3$-MaOH) containing 5% acetic acid. Anal. ($C_{11}H_{15}N_5O_3$+).25H$_2$O) C, H, N.

The ion-exchange column was eluted with 200 mL of 3 N acetic acid. Evaporation of the eluate followed by recrystallization from water gave 90.7 mg (43.2%) of chromatographically pure D-carbocyclic inosine, which was 100% pure by HPLC, mp 240° C. with shrinking from 237° C. (lt.mp (racemic) 225–227° C., 235° C.), $[α]^{23}_D$ –48.9 (C 0.2, DMF). Anal. ($C_{11}H_{14}N_4O_4$) C, H, N.

[1R,3S,4R-(1α,3β,4α)]-D-2-Amino-1,9-dihydro-9-[3-hydroxy-4-(hydroxymethyl)cyclopentyl]-6H-purin-6-one (D-2'-CdG)

Racemic carbocyclic 2,6-diaminopurine 2'-deoxyribofuranoside (350 mg, 1.32 mmol) was dissolved in 70 mL of 0.05 M phosphate buffer (pH 7.4) at 50° C. The solution was cooled to room temperature, ADA[250 µL containing 625 units (0.5 unit/µmol of (±)-C-2,6-DAPdR)] was added in one portion, and the progress of the reaction was monitored by HPLC. The deamination reaction had essentially stoped within 2 h, and the HPLC data indicated that the reaction solution contained approximately equal amounts of D-2'-CdG and L-2,6-diaminopurine 2'deoxyribofuranoside (C-L-2,6DAPdR). The reaction solution was heated at 100° C. for 3 min. to deactivate the enzyme, the mixture was filtered through Celite to remove agglutinated protein, and the filtrate was refrigerated when crystals began to form. D-2'-CdG was filtered off, washed with cold water, and dried in vacuo at 78° C.; yield, 80 mg (45%); mp 244–247° C. (inserted at 100° C., 3° C./min). Additional D-2'-CdG crystallized when the filtrate (including water washings) from the first crop was concentrated in vacuo to a final volume of 8 mL: yield after drying in vacuo at 78° C. for 2 h, 30 mg (17%, 2 crops); mp 244–246° C. (inserted at 100° C., 3° C./min). The analytical sample was obtained by combining the three crops of D-2'-CdG and recrystallizing (twice) from water: mp 242–245° C. (inserted at 100° C., 3° C./min); HPLC, $t_R$=6.3 min (99.8%); TLC, 1 spot (5:2:3

BuOH-HOAc-H$_2$O and 4:1 2-propanol-1 M NH$_4$OAc); MS (FAB), m/e266 (M+1): UV$_{max}$ 254 nm (11800) and 279 (8000) at pH 1,253 (13000 and 270–275 sh at pH 7,255–260 sh and 268 (11300) at pH 13; $[\alpha]^{23}_{546}$+5.5°, $[\alpha]^{23}_{576}$+4.80°, $[\alpha]^{23}_D$ +4.9±0.1° (c 1.0, 0.1 N NaOH). Anal. (C$_{11}$H$_{15}$N$_5$O$_3$•1.5H$_2$O) C, H, N.

[1S,3R,4S-(1α,3β,4α)]-L-2-Amino-1,9-dihydro-9-[3-hydroxy-4-(hydroxymethyl)cyclopentyl]-6H-purin-6-one (L-2'CdG)

A solution of 40 mg (0.15 mmol) of L-C-2,6-DAPdR and 240 μL of ADA (600 units, 4 units/μmol of 2b) in 80 mL of phosphate buffer (pH 7.5) was stirred at room temperature (18–22° C.) for 20 h. The deamination reaction was monitored by using the ammonium dihydrogen phosphate gradient eluting system. After 20 h, the ratio of L-C-2,6-DAPdR to L-2'CdG was about 2:1, and the reaction solution was then stirred at 37° C., HPLC indicated that the relative amounts of L-2'CdG and L-C-2,6-DAPdR to in the reaction soluton were 98% and 0.4%, respectively. The reaction mixture was heated at 100° C. for 3 min to deactivate the enzyme, the mixture was filtered through Celite to remove suspended protein, and the filtrate and water washings were combined and concentrated in vacuo to a volume of 7 mL. After crystals began to form, the mixture was refrigerated. The white crystalline product was filtered away, washed with cold water, and dried in vacuo at 78° C.; yield, 28 mg (70%); mp 238–241° C. (inserted at 135° C., 3° C./min). Recrystallization of this specimen from 2.2 mL of water afforded the analytical sample of L-2'CdG recovery, 26 mg (93%); mp 243–246° C. (inserted at 100° C., 3° C./min); HPLC, $t_R$=6.3 min (99.6%); TLC, 1 spot (5:2:3 BuOH-HOAc-H$_2$O and 4:1 2-propanol-1 M NH$_4$OAc); MS (FAB), m/e 266 (M+1); UV$_{max}$254 nm (11900), 279 (8100) at pH 1, 253 (12800) and 270–275 sh at pH7, 255–260 sh and 268 (11200) at pH 13; $[\alpha]^{16}_{546}$ −6.0°, $[\alpha]^{18}_{578}$ −5.5°, $[\alpha]^{16}_D$ −5.2° (c 1.0, 0.1 N NaOH). Anal. (C$_{11}$H$_{15}$N$_5$O$_3$•1.5H$_2$O) C, H, N.

[1S,2R,4S-(1α,2β,4α)]-L-4-(2,6-Diamino-9H-purin-9-yl)-2-hydroxycyclopentanemethanol (L-C-2,6-DAPdR)

The filtrate from the isolation of D-2'-CdG was shown by HPLC analysis to contain L-C-2,6DAPdR and D-2'CdG in a ratio of about 85:15. The solution was diluted to 75 mL with water and was stirred for 1.5 h with 5 mL of an anion-exchange resin (Dowex 1-X8, OH form). HPLC analysis of the supernatant solution indicated that all of the remaining D-2'CdG had been absorbed on the resin. The mixture was filtered, and the filtrate (combined with the water washings) was chromatographed on a column that contained 30 mL of a cation-exchange resin (Bio-Rad AG 50W-X4, H$^+$ form). The column was washed thoroughly with water and was then eluted with 1 N aqueous ammonia. Product-containing fractions were identified by UV analysis of the column effluent and were concentrated in vacuo to crystalline L-C-2,6-DAPdR: yield, 100 mg (57%); HPLC, 99%.

Additional L-C-2,6DAPdR was obtained by extracting the Dowex 1-X8 resin used above with three 25-mL portions of boiling water: weight, 15 mg (9%); HPLC, 99.3%. The analytical sample was obtained as a white, crystalline solid by recrystallizing the combined crops of L-C-2,6DAPdR: recovery, 90 mg (78%); mp 210–213° C. dec (inserted at 100° C., 3° C./min); HPLC,$^{26}$ $t_R$=7.5 min (99.7%); TLC, 1 spot (5:2:3 BuOH-HOAc-H$_2$O and 4:1 2-propanol-1 M NH$_4$OAc); MS (FAB), m/e 265 (M+1); UV$_{max}$ 217 nm (22300), 253 (9500), and 291 (9900) at pH 1,215 (29000) and 245–250 sh, 255 (8200), and 280 (10500) at pH 7 and 13; $[\alpha]^{23}_{546}$ −5.9°, $[\alpha]^{23}_{578}$ −5.5°, $[\alpha]^{23}_D$ −4.8° (c 1.0, H$_2$O). Anal. (C$_{11}$H$_{16}$N$_6$O$_2$•0.25H$_2$O) C, H, N.

Results

The antiviral activity of a number of guanine derivatives including acyclovir and related acyclic compounds has been attributed to their phosphorylation, a reaction that is believed to be catalyzed by a virus-encoded nucleoside kinase. For example, in viruses which produce viral thymidine kinase, such as HSV, acyclovir is phosphorylated to the monophosphate form which is then converted by cellular kinases to acyclovir triphosphate. The ability of this triphosphate form to interfere with the viral DNA polymerase is believed to be a source of antiviral activity of this compound. (Fyfe et al., J. Biol. Chem. 252:8721, 1978; Chu et al., J. Heterocycl. Chem. 23:289, 1986; De Clercq et al., in: Progress in Medicinal Chemistry, Ellis et al., eds., Vol. 23, pp. 187–218, Elsevier, Amsterdam, 1986). The structure of 2'CdG is substantially different from the 9-acyclic derivatives of guanine, and it is by no means certain that the presence of a virus-encoded kinase is essential to 2'-CdG activity. However, viral kinase, when present, appears to be involved in 2'-CdG activity. We therefore examined the interaction of racemic 2'CdG and its D- and L-enantiomers with HSV thymidine kinase.

Interaction of D-2'CdG, L-2'CdG, and D,L-2'CdG with HSV Thymidine Kinase

HSV thymidine kinase (HSV TK) was isolated from from HELA (BU25) cells infected with the SW148 strain of HSV-1 at a multiplicity of infection of 10 CCID$_{50}$ (1 CCID$_{50}$=the number of virions required to infect 50% of the cells) as described by Balzarini et al. (Mol. Pharmacol. 37:395, 1992). Both enantiomers of 2'CdG were tritiated by Moravek Biochemicals (Brea, Calif.) to yield [8-$^3$H]-D-2'CdG (250 mCi/mmole) and [8-$^3$H]-L-2'CdG (900 mCi/mmole). The samples had an initial radiopurity of greater than 99%. [Methyl-$^3$H]-thymidine (70–85 Ci/mmole) was obtained from Amerxham Corp. (Arlington Heights, Ill.). 9-Benzyl-9-deazaguanine was synthesized in our laboratories. Pyruvate kinase, dGuo, dCyd and mycophenolic acid were obtained from Sigma Chemical Co. (St. Louis, Mo.). HeLa (BU25) cells, a line deficient in thymidine kinase, were provided by Dr. Y.-C. Cheng (Yale University) and were maintained in Eagle's minimal essential medium supplemented with bovine calf serum. The S148 strain of HSV-1 was maintained in H.Ep.-2 cells as described previously (Bennet et al. Biochem. Pharmacol. 48:1515, 1990).

The purified HSV TK was incubated with various concentrations of radiolableled nucleoside. The HSV TK was incubated for 1 hour at 37° in 50 μl volumes containing 5.0 mM ATP, 5 mM MgCl$_2$, 9 mM potassium fluoride, 5 mM phosphoenol pyruvate, 2.8 μg of pyruvate kinase, 10 mM β-mercaptoenthanol, and various concentrations of unlabeled and labeled nucleosides (1, 1.25, 1.5, 2, 2.5, 3.33, 5, 6.66, 8, 10, 12.5, 15, 20, 33.3, 50, or 100 μM D-2'CdG; 1, 1.25, 1.5, 2, 2.5, 3.33, 5, 6.66, 8, 10, 12.5, 15, 20, 33.3, 50, or 100 μM L-2'CdG; 0.1, 0.125, 0.15, 0.2, 0.25, 0.33, 0.4, 0.5, 0.66, 0.8, or 1.0 μM thymidine). The reactions were terminated by spotting onto DE-81 discs (Whatman Lab Sales, Hillsboro, Ore.), after which the disks were washed with 100% ethanol. The radioactivity remaining on the disk (nucleoside monophosphate) was determined by transferring the disk to a vial, adding Scinti-Verse (Fisher Scientifi co., St. Louis, Mo.) and counting in a Packard Tri-Carb liquid scintillation spectrometer (Packard, Cowners Grove, Ill.).

Figure 1A:
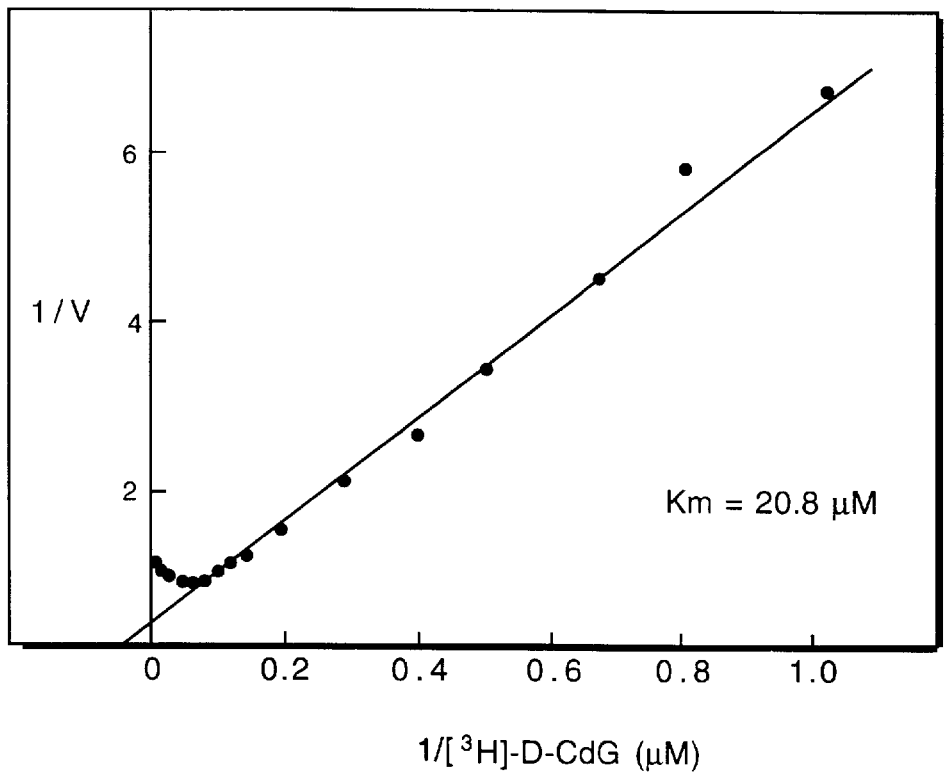
FIG. 1 depicts Lineweaver-Burk and Dixon plots the phosphorylation of D-2'CdG and L-2'CdG by partially purified HSV•TK.
Figure 1B:
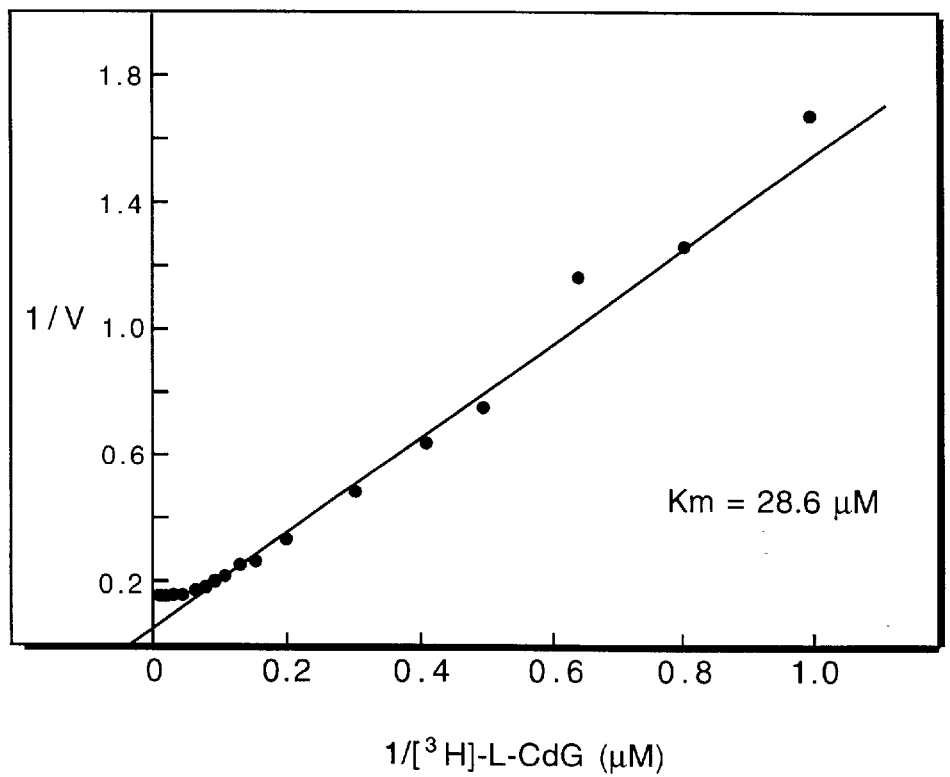

Lineweaver-Burke plots for both enantiomers demonstrated non-linear kinetics at the higher concentrations (FIG. 1). The lines were extrapolated from the linear portions of the double reciprocal plots to obtain $K_m$ values. Table 1 presents a summary of the kinetic constants for the enantiomers of 2'CdG and also for thymidine. The $K_m$ and $V_{max}$ values for L-2'CdG did not differ significantly from those for D-2'CdG. The $K_m$ values for the 2'CdG enantiomers were much higher than that for dThd and the $V_{max}$ values were about 50% greater than that for dThd.

TABLE 1

| Compound | $K_m$ ($\mu$M) | $V_{max}$ (nmole/hour/mg protein) |
|---|---|---|
| dThd | 0.31 | 8.7 |
| D-2'CdG | 20.8 | 12.6 |
| L-2'DdG | 28.6 | 13.4 |

To measure inhibition by the different forms of 2'CdG, thymidine kinase was incubated with [$^3$H]-thymidine alone or in the presence of D-2'CdG, L-2'CdG, or D,L-2'CdG. The phosphorylation of thymidine was determined by spotting the reaction mixture onto DE-81 filters, washing away unreacted substrate with ethanol, and determining the radioactivity ([$^3$H]TMP) remaining on the filters.

Figure 2A:
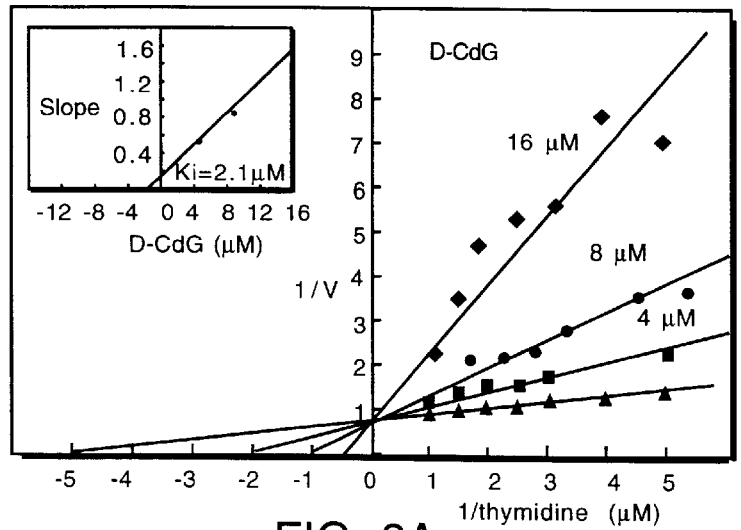
FIG. 2 depicts Lineweaver-Burk and Dixon plots of the effects of D-2'CdG, L-2'CdG, and D,L-2'CdG on the phosphorylation of [$^3$H-methyl]thymidine by partially purified HSV.TK.
Figure 2B:
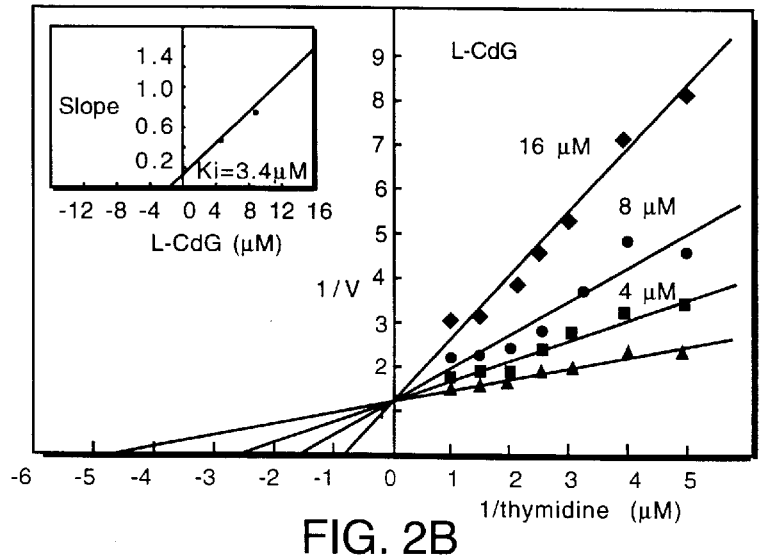
Figure 2C:
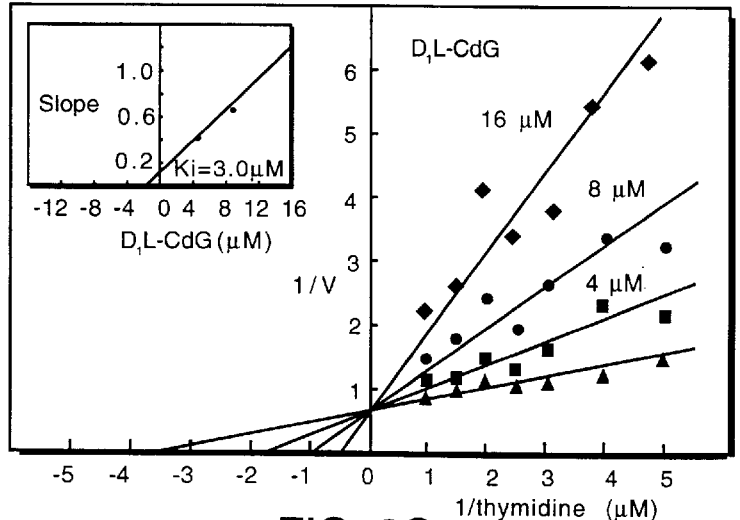
Figure 3A:
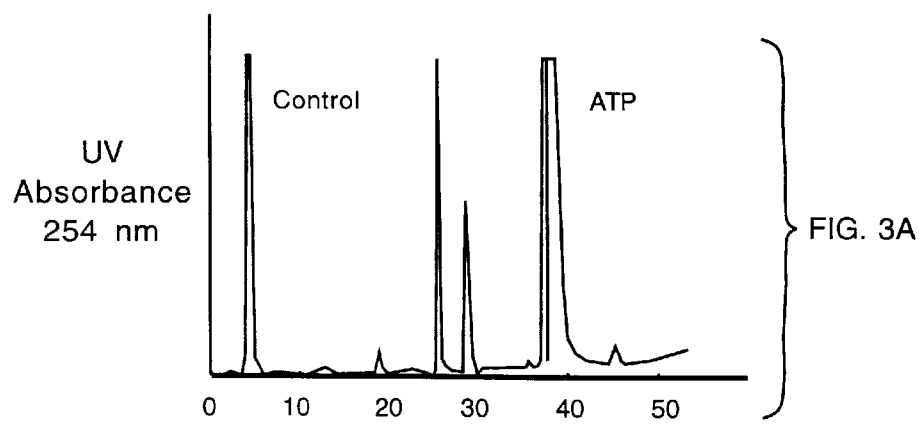
FIG. 3 illustrates the HPLC analyses of the phosphorylated products of racemic 2'CdG and its enantiomers by partially purified HSV.TK.
Figure 3B:
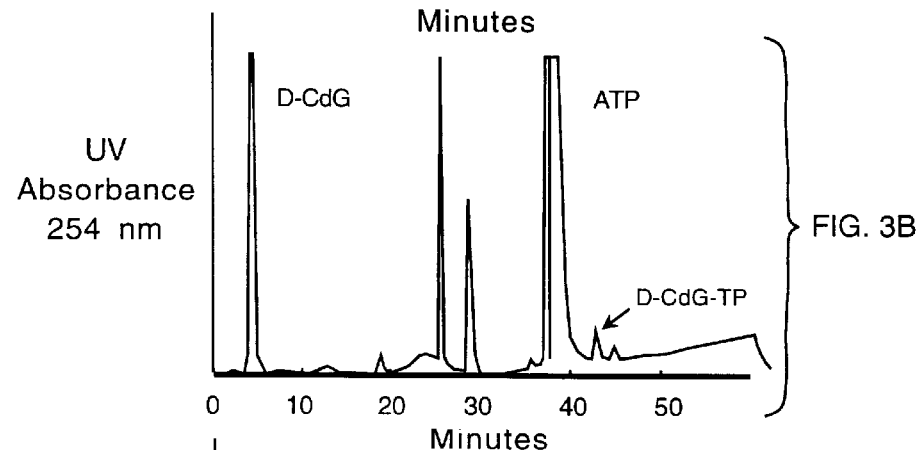
Figure 3C:
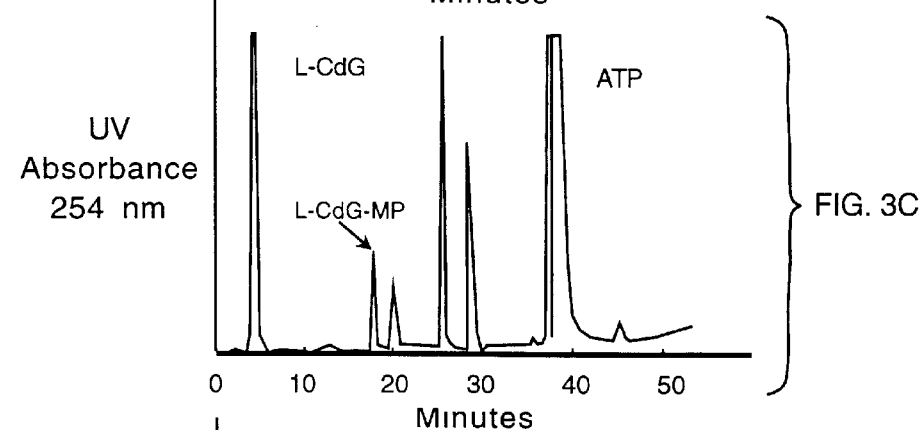
Figure 3D:
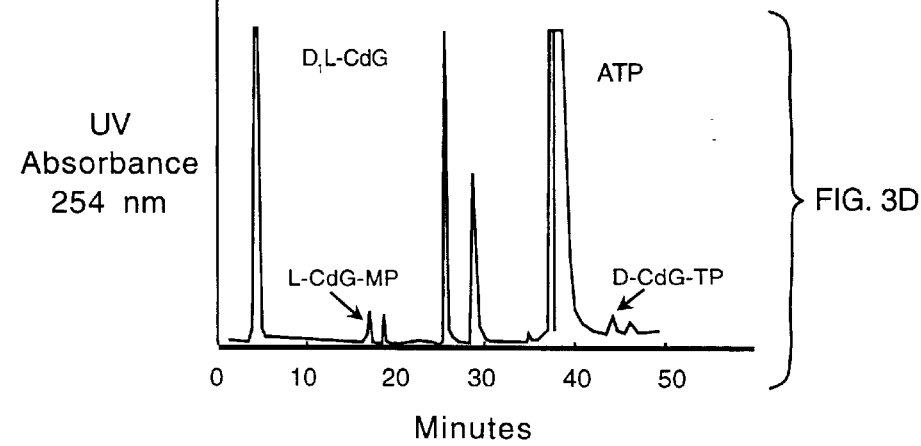

Both enantiomers of 2'CdG competitively inhibit the phosphorylation of thymidine by the partially purified HSV-1 TK (FIG. 2). The $K_i$'s were determined from a plot of the slope of each line versus the concentration of the competitor (D-, L, or D,L-2'CdG) and are summarized below:

TABLE 2

| Compound | $K_i$ |
|---|---|
| D-2'CdG | 2.1 $\mu$M |
| L-2'CdG | 3.4 $\mu$M |
| D,L-2'CdG | 3.0 $\mu$M |
| dGuo | 10.5 $\mu$M |

These data demonstrate that each of the enantiomers as well as the racemic mixture of 2'CdG are substrates for HSV thymidine kinase and competitively inhibit the phosphorylation of thymidine by HSV thymidine kinase at similar levels.

Phosphorylation of D-, L, and D,L-2'CdG

The assays discussed above were accomplished by the disk method which measures total radioactivity retained on the disk. Because of the unexpected finding that the L-enantiomer of 2'CdG was as good a substrate as the D-enantiomer, it was desirable to examine nucleotide formation by another method.

HSV thymidine kinase activity was measured in 200 $\mu$l volumes containing HSV-TK extract obtained as described previously (Belzarini et al., supra), 5.0 mM ATP, 5 mM MgCl$_2$, 9 mM potassium fluoride, 11.2 $\mu$g phosphoenol pyruvate, 5 $\mu$g of pyruvate kinase, 10 mM β-mercaptoethanol and either 50 $\mu$M [$_3$H]-D-, L, or no drug for 60 minutes at 37° C. The reaction was stopped with perchloric acid (PCA), neutralized with potassium bicarbonate, and the reaction products were analyzed by SAX HPLC. The UV absorption spectra of selected peaks were determined with a rapid spectral detector (LKB, Gaithersburg, Md.). The monophosphate and triphosphate derivatives were detected by absorbance at 254 nm. The data (FIG. 3) demonstrates that L-2'CdG is phosphorylated primarily to the monophosphate form (L-2'CdG-MP) whereas the major phosphorylated derivative of D-2'CdG is the triphosphate (D-2'CdG-TP). The amount of monophosphate derived from L-2'CdG was about the same as the amount of triphosphate derived from D-2'CdG, and confirmed the results of the disk assay. From these results, one would expect that the racemate would yield approximately equal amounts of monophosphate and triphosphate, and this was, in fact, the case.

HSV extracts were also incubated with 10 $\mu$M of either [$^3$H]-D- or L-2'Cdg, as described above, to measure the metabolism of these entantiomers. After 2 hours the reaction was stopped with perchloric acid (PCA), neutralized with potassium bicarbonate, and the acid-soluble metabolites were separated using SAX HPLC as described above. The results are summarized below.:

TABLE 3

| Compound | DPM | | | | |
| | nucleoside | mono | di | tri | total |
|---|---|---|---|---|---|
| D-2'CdG | 38555 | 2138 | 2427 | 85073 | 128000 |
| L-2'CdG | 40944 | 115000 | 2050 | 410 | 158000 |

The in vivo metabolism of D- and L-2'CdG was also measured in HSV-[TK+]-infected, HSV-[TK-]-infected and mock infected H.Ep.-2 cells (human epidermal carcinoma cells, ATCC CCL23). Uninfected and infected cells were incubated in fresh medium containing 2 $\mu$Ci/ml of either [$^3$H]-D- or L-2'CdG, as described above, to measure the metabolism of these entantiomers. After 8 hours the cells were harvested and washed free of medium with PBS, and extracts were prepared with cold 0.5 N perchloric acid for 0.5 hr. The extract was then neutralized with potassium bicarbonate and the resulting precipitate was removed by centrifugation. The supernatant was lyophilized to dryness and the acid-soluble metabolites were separated using SAX HPLC as described above.

Figure 4:
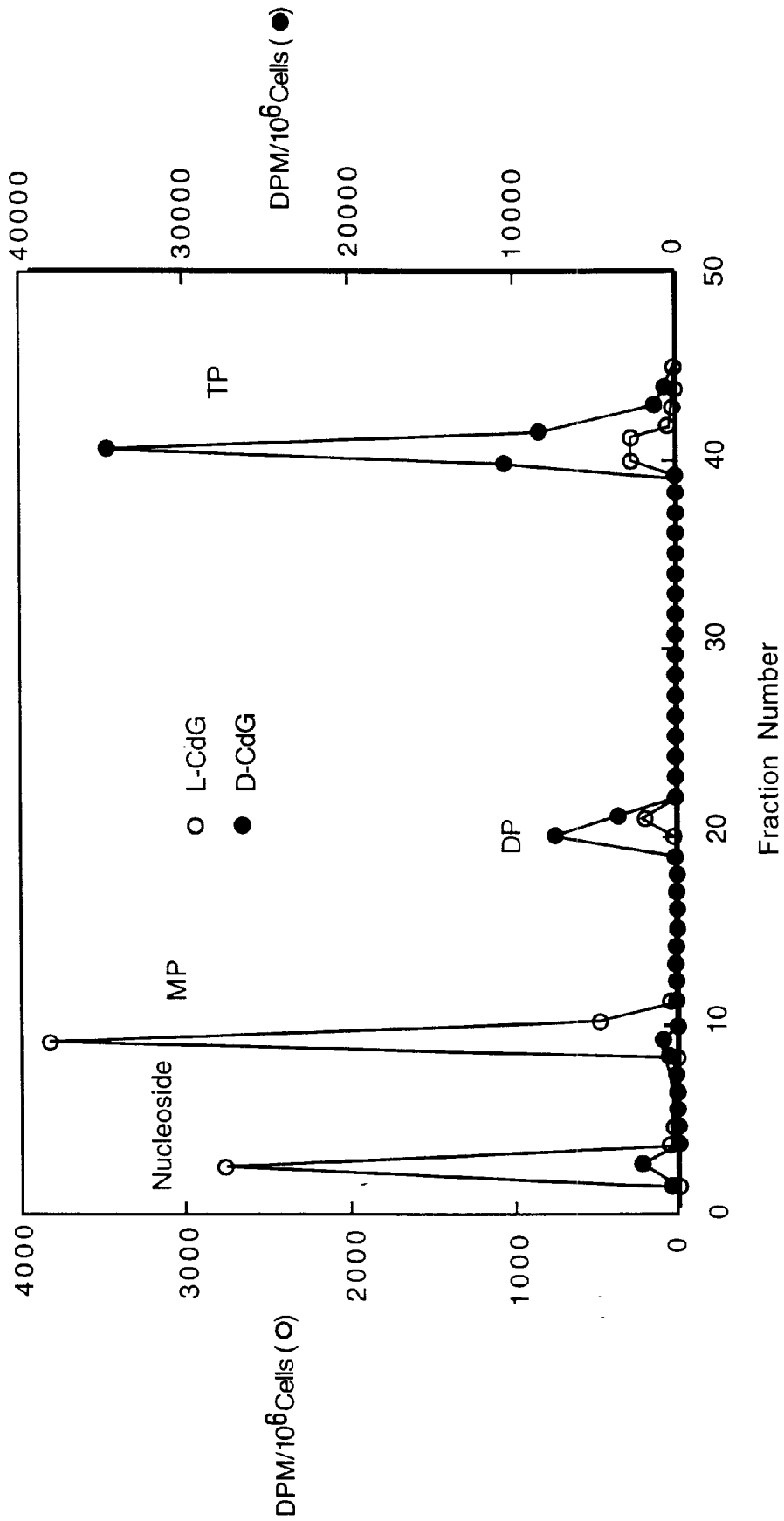
FIG. 4 illustrates the metabolic products of [$^3$H]-L-2'CdG and [$^3$H]-D-2'CdG in H.Ep.-2 cells infected with the S148 Strain of HSV-1.
Figure 5:
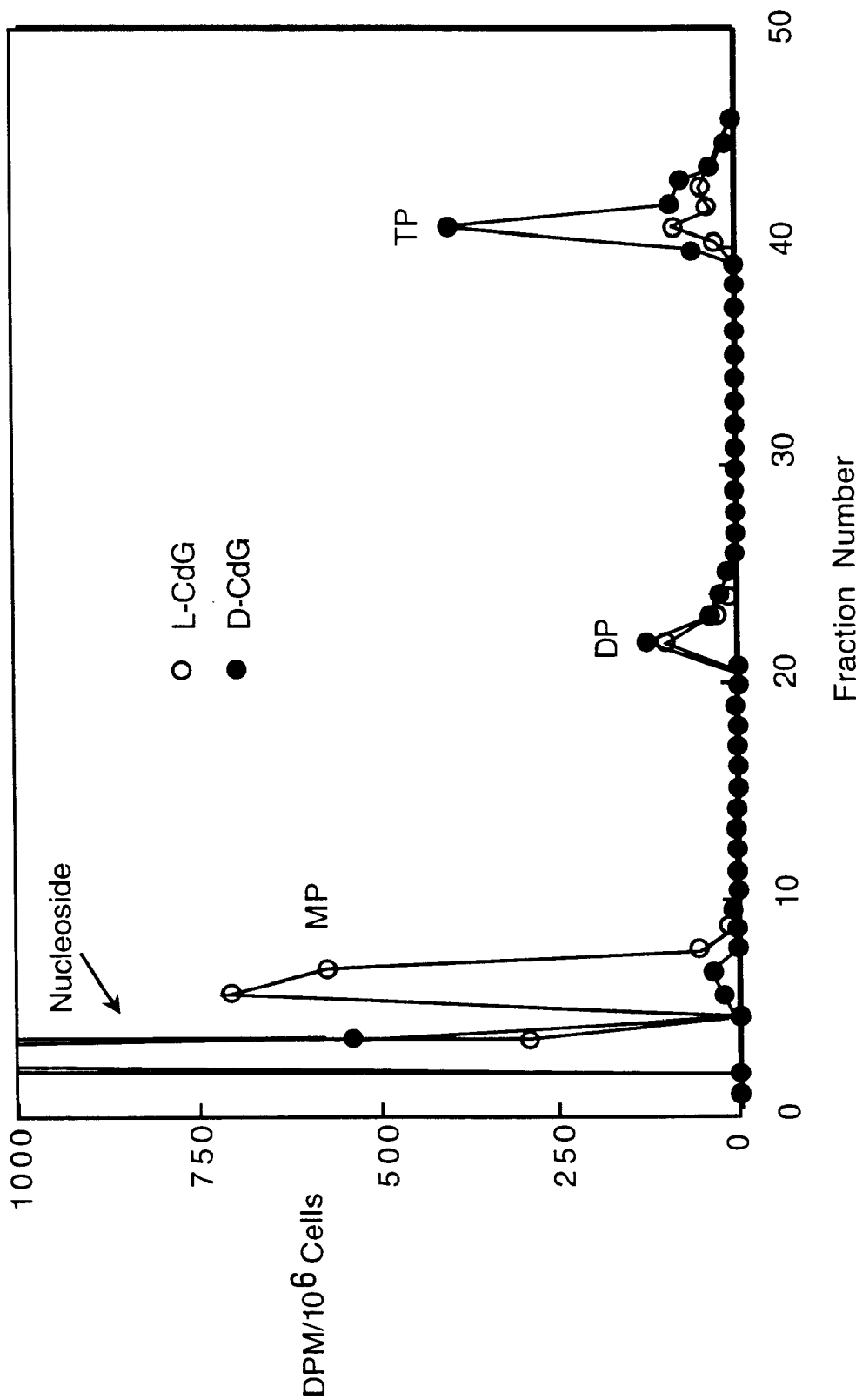
FIG. 5 depicts the metabolic products of [$^3$H]-D-2'CdG and [$^3$H]-L-2'CdG in CCRF-CEM cells.

In H.Ep.-2 cells infected with HSV-1 the principal soluble metabolite of D-2'CdG was the triphosphate, and the principal metabolite of L-2'CdG was the monophosphate (FIG. 4). While these findings are similar to those obtained with the isolated viral kinase, they differ from the resulted with the isolated enzyme in that relatively more di- and triphosphate were formed from L-2'CdG. In uninfected CEM cells, the total amounts of phosphates formed from either enantiomer were much less than in infected cells, and again the predominant metabolite of L-2'CdG was the monophosphate, whereas the predominant metabolite of D-2'CdG was the triphosphate. The total amount of phosphates of L-2'CdG formed in these cells was about twice that formed from D-2'CdG (FIG. 5); thus L-2'CdG appears to be superior to D-2'CdG as a substrate from one or more cellular phosphorylating enzymes.

Figure 6A:
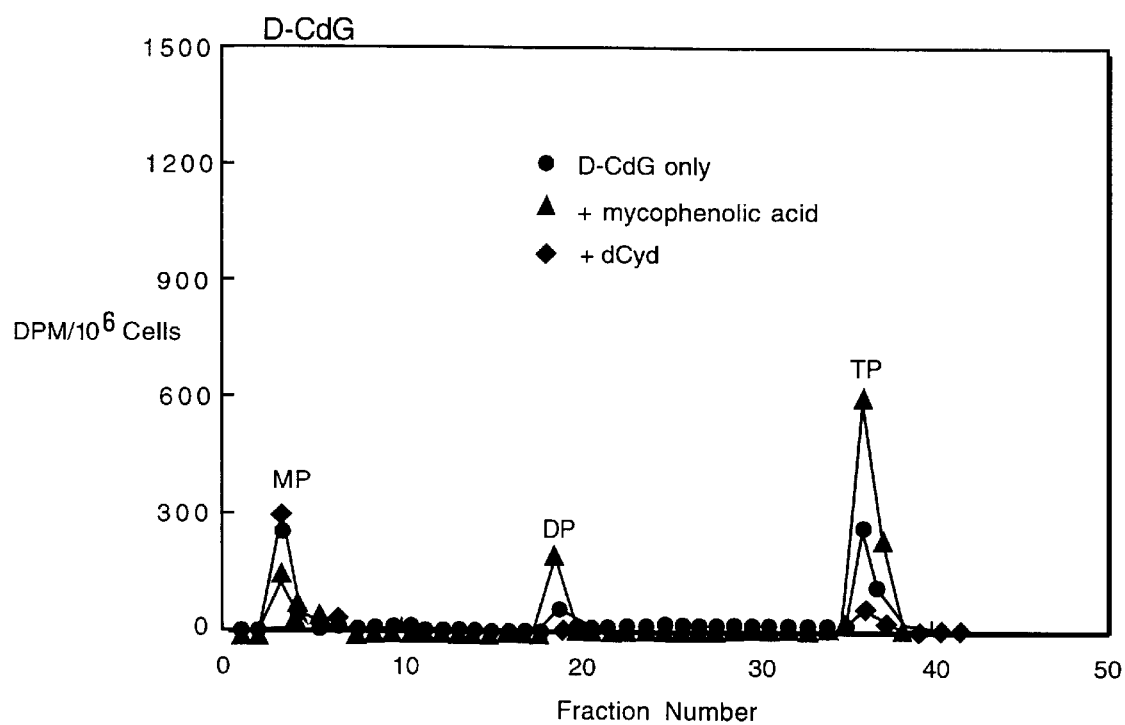
FIG. 6 illustrates the effects of dCyd and mycophenolic acid on the phosphorylation of D-2'CdG and L-2'CdG in CCRF-CEM cells.
Figure 6B:
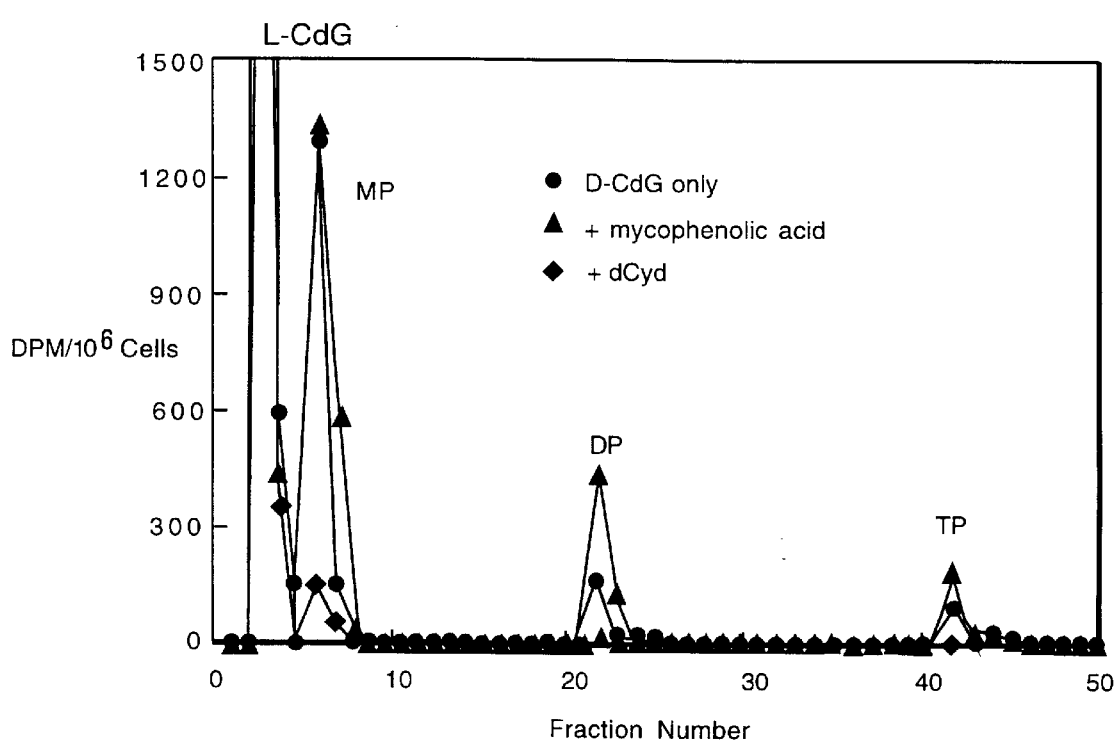

Identity of the Cellular Enzyme(s) Responsible for the Phsophorylation of the Enantiomers of 2'CdG The cellular enzymes most likely to catalyze the phosphorylation of 2'CdG to the monophosphate form are dCyd kinase, which appears to the principal enzyme responsible for the phosphorylation of dGuo in mammalian cells (Sarup et al., Biochemistry 26:590, 1987; Hurley et al., J. Biol. Chem. 258:15021, 1983), and 5'-nucleotidase, which has been shown to catalyze phosphorylation of several nucleoside analogs including 2',3'dideoxyinosine, carbovir, and acyclo derivatives of guanine (Keller et al., J. Biol. Chem. 260:8664, 1985; Bondoc et al., Biochemistry 29:9839, 1990; Johnson et al., Mol. Pharmalcol. 36:291, 1989). To determine if dCyd kinase was involved, studies were carried out in which cells were indubated with D- or L-2'CdG and dCyd, and the formation of phosphates was monitored by HPLC. To determine if 5'nucleotidase was involved cells were incubated with D- or L-2'CdG or mycophenolic acid, which has been shown to increase the activity of this enzyme by producing a buildup of IMP (Ahluwalia et al., *Biochem. Biophys. Res. Communs.* 171;1297, 1990; Hartman et al. Mol. *Pharmac.* 40:118, 1991). As shown in FIG. 6, the presence of dCyd markedly decreased the amount of phosphates of both D- or L-2'CdG; the reduction, calculated from the radioactivity in the peaks, was 80–90% for both enantiomers. The presence of mycophenolic acid produced an increase in the phosphates of D- or L-2'CdG of 2.5-fold and 1.4-fold, respectively. These results indicate that dCyd kinase may be the principal enzyme responsible for catalyzing the initial phosphorylation of both enantiomers, although the participation of 5'-nucleotidase as well as other, as yet unidentified enzymes, is not excluded. The fact that the presence of mycophenolic acid increases the phosphorylation of both enantiomers (FIG. 6) would suggest the involvement of 5'-nucleotidase. However, an alternative interpretaion of these data would be that mycophenolic acid, by lowering the concentrations of guanine nucleotides, decreases the normal feedback control of dCyd kinase.

It is likely that the enzyme responsible for the phosphorylation of the D-2'CdG-MP is human guanylate kinase that co-purifies with the HSV TK. Alternatively, the HSV TK also contains a monophosphate kinase and it is possible that this enzyme is responsible for the phosphorylation of D-2'CdG-MP. In turn, D-2'CdG-DP could be phosphorylated by either human nucleoside diphosphate kinase, which co-purifies with the HSV-TK, or the pyruvate kinase which is a component of the assay.

Comparison of dGuo and 2'CdG as Substrates for HSV-1 TK

Figure 7:
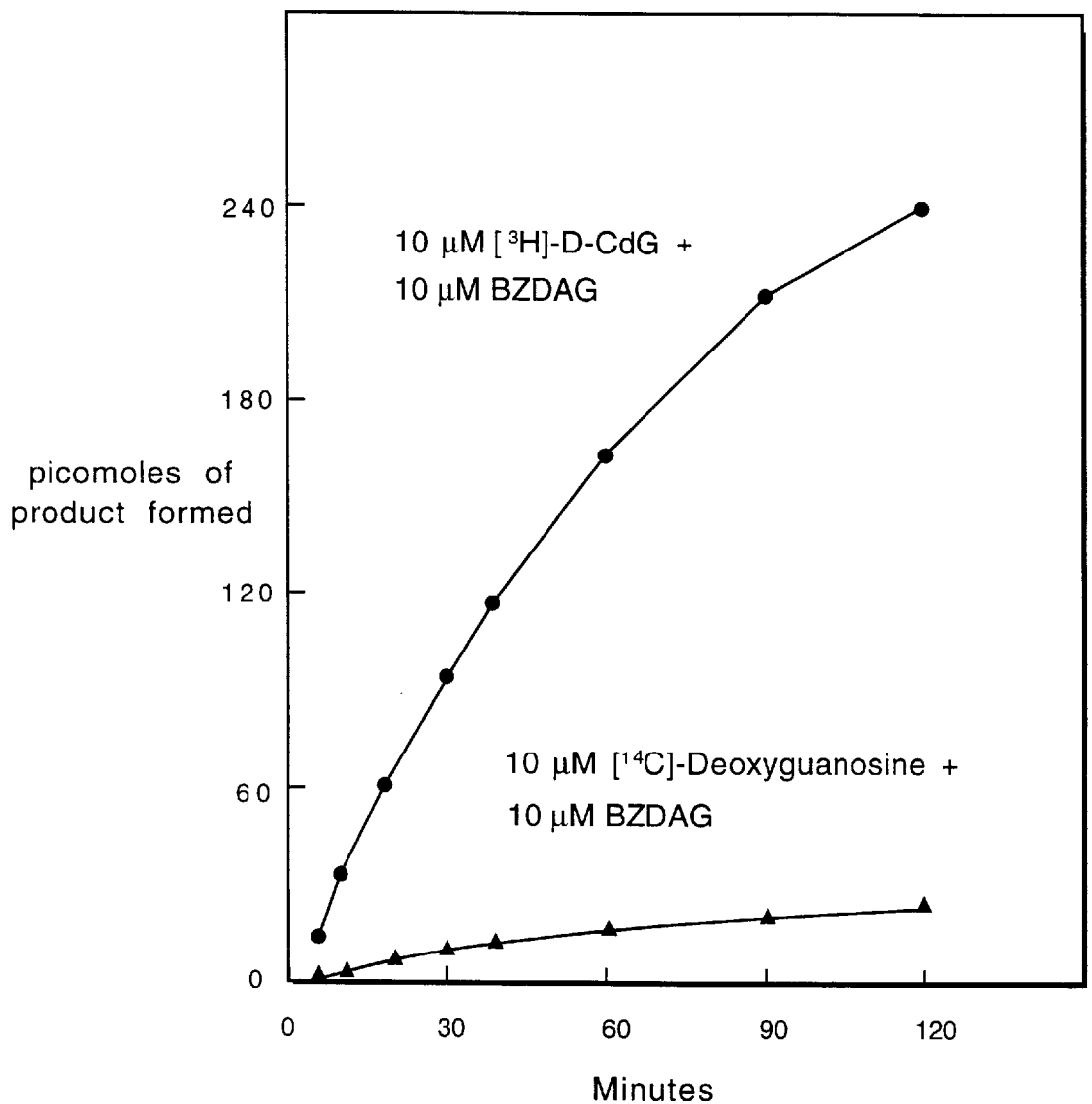
FIG. 7 is a graph which compares D-2'CdG and dGuo as substrates for partially purified HSV•TK.

It was of interest to compare 2'CdG and its natural counterpart, dGuo, as substrates for the viral kinase. since preparation of the viral enzyme was only partially purified, it was necessary to take into account the possible presence of interfereing enzymes. The kinase preparation was in fact found to contain some purine nucleoside phosphorylase (PNP) activity. Therefore, we added 9-benzyl-9-deazaguanine (BzDAG), a potent inhibitor of PNP, to the incubation mixture. The phosphorylation of 2'CdG proceeeded at a rate much higher than that for dGuo (FIG. 7). Similar experiments performed in the absence of BzDAG yielded about the same results with D-2'CdG and showed, at best, a slight decrease in the rate of phosphorylation of dGuo. Thus, although PNP activity was present in the enzyme preparation, it did not have a significant effect on the phosphorylation of dGuo. Although it has been reported that dGuo is a poor substrate for this enzyme (Fyfe et al., *J. Biol. Chem.*, 253:8721, 1978), it is unexpected that the replacement of the 4'-O atom by a methylene group would improve substrate activity so markedly.

As was previously discussed, the inhibitory forms of many antiviral nucleosides are the triphosphates, and the target is the virus-coded DNA polymerase. Activity of nucleoside analogs for viral inhibition may therefore be determined by the potency of the triphosphate forms as inhibitors of the viral polymerase. Therefore, we analyzed the effects of D-2'CdG on the viral and host DNA polymerases.

Incorporation of [$^3$H]-D-2'CdG into HSV and Host DNA

Mock-infected and HSV-infected cells tretated with the desired label were collected by centrifugation. The cell pellet was resuspended in 0.5 ml of 10 mM Tris, pH 8.0, 40 mM EDTA, 0.5% sodium dodecyl sulfate, 200 µg/ml proteinase K, and the mixture was incubated at 37° overnight. One hundred microliters of each sample wre mixed with 5.0 ml of a CsCl solution, such that the final concentration of the CsCl was 1.75 g/ml. Host DNA labeled with [$^{14}$-C]dThd was included in each sample as an internal control. The samples were centrifuged to equilibrium at 20° (30,000 rpm for 72 hr, with a Ti 70.1 Beckman rotor). Twenty-five microliter fractions were collected from the top of each gradient, and the DNA in each fraction was precipitated onto glass fiber filters with a 5% trichloroacetic acid solution containing 10 mM pyrophosphate. These filters were washed three times with this solution followed by two washes with 95% ethanol and dried. The radioactivity in the acid-insoluble portion in every fourth fraction of each gradient was then determined and plotted in relation to its internal standard, the $^{14}$C-labeled host DNA.

To verify that the radioactivity associated with both the host and viral DNA peaks was due to the incorporation of [$^3$H]-D-2'CdG, the DNA samples were pooled, dialyzed against water to remove the CsCl, lyophilized, and resuspended in 50 µl of DNase I in 50 mM glycine, pH 9.0. After incubation for 2 hr at 37° C., 50 µl of 100 units/ml concentrations of both phosphodiesterase I and alkaline phosphatase in 50 mM glycine, pH 9.0 were added to each sample, and the reaction was stopped by boiling for 2 min, the precipitated porteins were removed by centrifugation, and the samples were analyzed by reverse phase HPLC for the appearance of radiolabeled nucleoside. To determine whether the [$^3$H]-D-2'CdG was incorporated into internal or terminal positions, the DNA after the lyophilization step was digested by the sequential action of micrococcal nuclease (50 units/ml micrococcal nuclease, 5 µg/ml pentostatin, 5 mM CaCl$_2$, 1 mM Tris, pH 9.5, for 2 hr at 37° C.) and spleen phosphodiesterase (three consecutive additions of 75 µg/ml spleen phosphodiesterase, 1 mM EDTA, in the same buffer at pH 7.0, for 1 hr each time at 37° C.), as described by Pelling et al. (Virology 109:323, 1981). These enzymes specifically cleave RNA and DNA to generate 3'-monophosphates of all internally located nucleotices and the nucleoside of any 3'-terminal nucleotides. After digestion, the samples were analyzed by strong anion exchange HPLC, to separate monophosphates from nucleosides.

The incorporation of [$^3$H]-D-2'CdG into the DNA of cells infected with HSV was determined at various times after infection to optimize conditions for the incorporation of D-2'CdG into either HSV or host DNA. When HSV-infected cells were incubated for 9 hr with 8 µM [$^3$H]-D-2'CdG, starting at thte time of infection (FIG. 8), label was found only in host DNA. Very little incorporation of [$^3$H]-D-2'CdG into DNA was observed in cells that were not infected with virus. These results indicated that [$^3$H]-D-2'CdG-TP formed from the sequential action of the HSV TK and host nucleotide kinases was then utilized by a host DNA polymerase for DNA synthesis. When HSV-1-infected cells were treated for 5 hr with 1 µM [$^3$H]-D-2'CdG, starting 4 hr after infection (FIG. 2), label was found primarily in viral DNA. The small amount oflabel in the host DNA is presumably due to the near-total inhibition of host DNA synthesis by 4 hr of the viral infection. The lack of label in viral DNA incubated with [$^3$H]-D-2'CdG from 0 to 9 hr of virus infection was probably due to effective inhibition of viral replication by drug treatment (8 µM 2'CdG is 10 times the concentration required to inhibit viral replication by 50%). Although [$^3$H]-D-2'CdG is undoubtedly incorporated into viral DNA under these conditions, the amount of incorporation is below the level of detection.

The density of viral DNA labeled with 1.0 µM [$^3$H]-D-2'CdG was the same as that seen with [$^3$H]Thd-labeled viral DNA. However, if the concentration of [$^3$H]-D-2'CdG was increased to 8 µM, the density of the labeled DNA was decreased, so that the viral DNA banded between the host and viral DNA markers. The reason for this shift in the binding in the CsCl gradient is not known. However viral DNA obtained from HSV-infected cells treated with 8 μM [$^3$H]-D-2'CdG sedimented in either neutral or alkaline sucrose gradients, prepared according to standard methods (McGuirt et al., Antimicrob. Agents Chemother. 25:507, 1984; Balzarini et al., Mol. Pharmacol. 37:402, 1990), in a manner similar to that of viral DNA labeled with [$^3$H]dThd, indicating that the viral DNA containing 2'CdG was the same size as viral DNA from untreated cells.

The nucleosides of the radioactive viral and host DNAs were then analyzed using reverse phase HPLC as described above. All of the radioactivity in the DNA eluted from the reverse phase column with authentic 2'CdG, confirming that the radioactivity in the DNA was due to the incorporation of 2'CdG. The viral and host DNA labeled with [$^3$H]-D-2'CdG were also degraded with micrococcal nuclease and spleen phosphodiesterase I, to generate 3'-monophosphates of all internally located nucleotides and the nucleosides of any terminal nucleotides. The nucleosides and nucleotides were then analyzed by strong anion exchange chromatography. Most of the radioactivity in both the viral and host DNA was converted to the 3' monophosphate of D-2'CdG-Mp, indicating that D-2'CdG was incorporated into internal linkages by the HSV DNA polymerase and the host polymerase responsible for incorporation. The percentage of D-2'CdG incorporated into internal linkages in the DNA chain was the same as that seen in similar experiments using [$^3$H]dThd to label the DNA.

Inhibition of purified HSV and host DNA polymerases by 2'CdG-TP. Because D-2'CdG was incorporated into both HSV and host DNA, the interaction of 2'CdG-TP with the HSV and host DNA polymerases was studied.

HSV DNA polymerase was purified from H.Ep.-2 cells infected with HSV-1. Approximately 4×10$^8$ cells were infected with virus at a multiplicity of infection of 10 CCID$_{50}$/cell. After a 1 hr adsorption period, the unattached virus was waxhed from the cells and the cultures were returned to the incubator at 37° C. for another 8 hr. The cells were collected by centrifugation and mixed with a 0.3 M potassium phosphate buffer, pH 7.5, containing 0.3% Triton X-100 and 10% glycerol. The HSV DNA polymerase was purified approximately 288-fold from this crude extract, as described by Derse et al. (J. Biol. Chem. 257:10251, 1982). The specific activity of the HSV DNA polymerase was 4140 units/mg protein. Human DNA polymerases, α, β, and γ, were purified from 5.0 ml of packed K562 cells grown in cell culture as previously described (Parker et al., J. Biol. Chem. 266:1754, 1991). The specific activities of DNA polymerases α, β, and γ used in these studies were approximately 34, 1600, and 8 units/mg protein, respectively. One unit of enzyme activity is defined as the amount of enzyme needed to incorporate 1 nmol of [$^3$H]dGTP into acid-precipitable material per hour at 37° C., using gapped DNA as a template. HSV DNA polymerase activity was measured in 50 μl volumes containing 50 mM Tris, pH 8.0, 3 mM MgCl$_2$, 0.5 mM dithiothreitol, 0.2 mg/ml bovine serum albumin, 0.2 M KCl, 12.5 μg/ml gapped DNA, 10 μM [$^3$H]dGTP (12 Ci/mmol), and 100 μM each of dATP, dCTP, and TTP. DNA polymerase a activity was measured in 50 μl volumes containing 50 mM Tris, pH 8.0, 1 mg/ml bovine serum albumin, 10 mM MgCl$_2$, 1 mM dithiothreitol, 100 μg/ml gapped duplex DNA, 10 μM [$^3$H]dGTP (1 Ci/mmol), and 50 μM of each dATP, dCTP and TTP. DNA polymerase β and γ activities were measured as described for DNA polymerase α, except that the reactions included 100 mM KCl. After incubation for the desired time, the DNA in each sample was precipitated onto glass fiber filters using a 5% trichloroacetic acid solution containing 10 mM pyrophosphate. The filters were then washed three times with this solution followed by two washes with 95% ethanol, dried, and counted for radioactivity.

2'CdG-TP was a potent competitive inhibitor of the incorporation of [$^3$H]dGTP into DNA by both the HSV DNA polymerase and the host DNA polymerase α (FIG. 9). The average K$_i$ of D-2'CdG-TP against HSV DNA polymerase was 0.35 μM, and with DNA polymerase α it was 0.95 μM. The K$_i$/K$_m$ ratio for both DNA polymerases was approximately 1, indicating that the affinity of 2'CdG-TP for the active site of these enzymes was similar to that of dGTP.

Under similar incubation conditions, the concentration of D-2'CdG-TP required to inhibit the incorporation of 1 μM [$^3$H]dGTP into the DNA by 50% was 2 μM with DNA polymerase α, but was 2200 and 300 μM for DNA polymerase β and γ, respectively (Table 4). The L-enantiomer of 2'CdG-TP also inhibited DNA polymerase β and γ at concentrations similar to or less than that required for inhibition by the D-enantiomer.

TABLE 4

| | IC$_{50}$ | |
|---|---|---|
| | D-2'CdG-TP | L-2'CdG-TP |
| | μM | |
| HSV DNA polymerase | 1.5 | 460 |
| DNA polymerase α | 2.0 | 470 |
| DNA polymerase β | 2200 | 1400 |
| DNA polymerase γ | 300 | 215 |

Antiviral Activity of D-; L- and D,L-2'CdG

The antiviral activities of the racemate and each 2'CdG enantiomer were studied.

EXAMPLE 1

D-2'-CdG and L-2'-CdG were tested, alongside D,L-2'-CdG, against both HSV-1 (strain 377, TK+; obtained from Dr. Earl Kern, University of Alabama) and HSV-2 (strain MS, TK+; also obtained from Dr. Earl Kern). In these tests (Table 5), Ara-A and acyclovir (ACV) were the positive control drugs. In four tests vs. HSV-1, the antiviral activity (VR) and potency (MIC$_{50}$) of D-2'-CdG were approximately the same as those of racemic 2-CdG. L-2'-CdG was only modestly active.

D,L-2'-CdG and D-2'-CdG were more effective than was the positive control drug, Ara-A. D-2'-CdG, (D,L)-2'CdG, and ACV were comparable in antiviral activity, but the two forms of 2'CdG were 5–10 times more potent than was ACV.

These compounds were tested against HSV-2(TK$^+$). The VR of ACV was somewhat higher than the VR values of D-2'-CdG and D,L-2'-CdG, but the values of MIC$_{50}$ of the two forms of 2'-CdG were lower. In addition, experiments comparing the antiviral activity D-2'-CdG with acyclovir against HSV-1 in human foreskin fibroblasts have shown an even greater potency, in favor of D-2'-CdG.

TABLE 5

Activity of Enantiomers of 2'-CdG
Against Herpes Simplex Virus Types 1 and 2

| | HSV-1 | | HSV-2 | |
|---|---|---|---|---|
| Compound | VR | Mic$_{50}$ (µg/ml) | VR | Mic$_{50}$ (µg/ml) |
| D-2'-CdG | 4.8–6.3 | 0.1–0.3 | 3.8 | 0.7 |
| D,L-2'-CdG | 5.3–7.0 | 0.2–0.3 | 3.7 | 2.6 |
| L-2'-CdG | 0.8–2.4 | 39–257 | 0 | — |
| Ara-A | 1.6–2.5 | 10–34 | 1.3 | 50 |
| Acyclovir | 5.7–6.5 | 1.5–2.9 | 4.5 | 5.3 |

EXAMPLE 2

The D- and L-enantiomers of 2'-CdG were prepared from racemic C-2,6-DAPR by an enzymatic method as described above Secrist et al. (*J. Med. Chem.* 30:746, 1987). The effectiveness of racemic-2'-CdG and of D-2'-CdG in reducing CMV yields in MRC5 cell monolayer cultures was determined by a plaque assay with the results set forth in tables 6 and 7.

TABLE 6

THE EFFECT OF THE CARBOCYCLIC ANALOGUE OF 2' DEOXYGUANOSINE [(±-2'-CdG] ON CMV YIELDS IN MRC5 CELL MONOLAYER CULTURES

| (+-2'-CdG$^{1a}$ | Reduction (%) of CPE by CdG at Time of Harvest | CMV Yield (log$_{10}$CCID$_{50}$/mL) | Drug Cytotoxicity (Gross Morphology) |
|---|---|---|---|
| 32 µg/mL | — | — | toxic |
| 10 | 100 | 0 | sl. toxicity |
| 3.2 | 100 | 1.0 | v. sl. toxicity |
| 1.0 | 95 | 3.6 | 0 |
| 0.32 | 20 | 4.5 | 0 |
| 0.1 | 0 | 5.0 | 0 |
| 0.032 | 0 | 5.4 | 0 |
| 0 (Virus Control) | — | 5.5 | — |

[a]Drug treatment began immediately following the virus adsorption period (1 1/2 hr).

TABLE 7

THE EFFECT OF THE CARBOCYCLIC ANALOGUE OF D-2'-DEOXYGUANOSINE [D-2'-CdG] ON CMV YIELDS IN MRC5 CELL MONOLAYER CULTURES

| D-2'CdG$^a$ | Reduction (%) of CPE by D-2'CdG at Time of Virus Harvest | CMV Yield PFU/mL | log$_{10}$ PFU/mL | Drug Cytotoxicity (Gross Morphology) |
|---|---|---|---|---|
| 320 µM | — | — | — | toxic |
| 100 | 50 | 0 | — | slight toxicity |
| 32 | 50 | 0 | — | v. sl. toxicity |
| 10 | 25 | 2 × 10$^1$ | 1.3 | 0 |
| 3.2 | 10 | 8.4 × 10$^2$ | 2.9 | 0 |
| 1.0 | 10 | 5.4 × 10$^3$ | 3.7 | 0 |
| 0.32 | 0 | 1.4 × 10$^4$ | 4.1 | 0 |
| 0.1 | 0 | 3.8 × 10$^4$ | 4.6 | 0 |
| 0 (Virus Controls) | — | 1.1 × 10$^5$ | 5.1 | — |

[a]Drug treatment began immediately following the 1 1/2 hour virus adsorption period.

The MIC$_{50}$ of D-2'-CdG (<0.029 µL/mL) was about half (or less) of the MIC$_{50}$ of D,L-2'-CdG (0.069 µg/mL) measured under the same conditions in MRC5 cells.

EXAMPLE 3

The in vitro activity of D-2'-CdG was also compared with the current investigational drug of choice for human CMV, DHPG. These experiments were carried out in human foreskin fibroblast cells. The ED$_{50}$ value (median dose at which 50% antiviral efficacy is observed) was 0.06 µg/ml for D-2'-CdG and 0.20 for DHPG, demonstrating that that the antiviral potency of D-2'-CdG is more than 3 times that of DHPG.

EXAMPLE 4

New Zealand white rabbits were found to develop reproducible clinical symptoms of infection within 3–4 days after intravitreal inoculation with human CMV. The symptoms included vitritis, iritis, retinal pathology (micro hemorrhages and focal necrosis of the retinal surface), corneal stromal haze and neovascularization, and corneal endothelial pigmented precipitates. Administration of D-2'-CdG by intravitreal injection, i.e., by injection directly within the vitreous humor (100 µg in 100 µl of sterile water) at 48-hour intervals beginning at day 4 was effective in reducing the develpment of retinal pathology and in reducing the severity of the vitritis and iritis as xompared to rabbits receiving a placebo. It was found that in most cases treatment with D-2'-CdG was clinically better than treatment with ganciclovir (DHPG) under the same conditions. The intravitreal route offers some significant advantages for intraocular infections including: 1) delivery of maximal concentrations of drug to the desired site of action; 2) increased potential for sustained release (i.e., longer half-life, T$_{1/2}$) of the drug; and 3) reduced potential for systemic toxicity.

EXAMPLE 5

2'-CdG was tested at three concentrations (50 ng/ml, 500 ng/ml, and 5 ug/ml) against the HBV-producing, human liver cell line, 2.2.15 (Sells et al., *J. Virol.* 62:2836, 1989). A racemic (D,L) preparation, as well as the purified D and L isomers were tested. For these analyses compounds were tested in duplicate at all concentrations. Ara-AMP and ddG (2'3'-dideoxyguanosine) were used as HBV inhibitory control compounds. Ara-AMP is a widely used compound in antiviral research and has been demonstrated to have activity against HBV in chronically infected patients (Alexander et al. *Brit. Ned. J.* 292:915, 1986). The nucleoside analog, ddG was used as an additional control compound since ddG has activity against duck hepatitis B virus in chronically infected Peking ducks (Lee et al., *Antimicrob. Agents Chemother.* 33:336, 1989) and 2'-CdG is also a deoxyguanosine analog.

2.2.15 cells were seeded in 6 well culture plates and grown to confluence over a 10 day period in medium with 5% FBS. Test compounds were then added daily for a continuous 10 day period in medium with 1% dialyzed FBS. This reduced serum level does not affect HBV replication in confluent cultures of 2.2.15 cells and helps to eliminate uncontrolled variations of endogenous low molecular weight compounds (such as nucleosides) present in FBS. Compounds were tested, in duplicate cultures, at 3 concentrations covering a 100-fold range. Culture medium (changed daily during the treatment period) was collected and stored for analysis of extracellular (virion) HBV DNA from days 0, 3, 6, and 10 of the treatment period. This allowed for an analysis of the level of HBV virion production during discrete 24 hour intervals and reduced the potential for the buildup of toxic metabolites derived from the test compounds. Treated cells were lysed following the 10th day of treatment for the analysis of intracellular HBV genomic forms. HBV DNA was analyzed in a quantitative manner for (i) overall levels (both extracellular and intracellular DNA) and (ii) the relative rate of HBV replication (intracellular DNA only).

HBV DNA levels were measured by comparison to known amounts of HBV DNA standards applied to every nitrocellulose filter (gel or slot blot) using an AMBIS Beta Scanner. Standard curves, generated by multiple analyses, the racemic mixture. The L isomer did not exhibit any significant anti-HBV activity at the concentrations tested.

No obvious toxicity was observed for any of the three compound preparations. Toxicity in these experiments was not quantitatively assessed. Toxicity was based upon the physical appearance of the cells (e.g. vacuolization, granulation, morphological changes, detachment of cells).

TABLE 8

Effect of test compounds on HBV production in 2.2.15 cell cultures.

| | | INTRACELLULAR HBV DNA (PG/UG CELL DNA) | | | HBV DNA IN CULTURE MEDIUM (PG/ML) | | | |
|---|---|---|---|---|---|---|---|---|
| WELL | TREATMENT | INTEG. | MONO. | RI | DAY 0 | DAY 3 | DAY 6 | DAY 10 |
| 25A | UNTREATED CELLS | 1.4 | 3.0 | 53 | 50 | 50 | 46 | 40 |
| 25B | " | 1.2 | 2.0 | 50 | 55 | 100 | 42 | 45 |
| 25C | ARA-AMP @ 300 UG/ML | 1.3 | 0.1 | 0.2 | 100 | 25 | 0 | 0 |
| 25D | " | 1.1 | 0.1 | 0.3 | 95 | 30 | 0 | 0 |
| 25E | DDG @ 100 uM | 1.6 | 0.2 | 0.1 | 49 | 35 | 8 | 0 |
| 25F | " | 1.7 | 0.1 | 0.1 | 58 | 41 | 2 | 0 |
| 25G | D,L 2-CdG @ 5 ug/ml | 1.6 | 1.7 | 0.1 | 88 | 24 | 0.4 | 0 |
| 25H | " | 1.0 | 1.9 | 0.3 | 87 | 16 | 0.3 | 0 |
| 25I | D,L 2-CdG @ 500 ng/ml | 1.4 | 1.8 | 0.4 | 89 | 41 | 8 | 0.1 |
| 25J | " | 1.5 | 2.0 | 1 | 90 | 55 | 17 | 0.2 |
| 25K | D,L 2-CdG @ 50 ng/ml | 1.3 | 2.1 | 12 | 120 | 88 | 55 | 11 |
| 25L | " | 1.2 | 1.4 | 18 | 95 | 75 | 77 | 6 |
| 25M | D, 2-CdG @ 5 ug/ml | 1.6 | 2.0 | 0.3 | 100 | 18 | 3 | 0 |
| 25N | " | 0.7 | 2.0 | 0.1 | 120 | 21 | 6 | 0 |
| 25O | D, 2-CdG @ 500 ng/ml | 1.0 | 1.9 | 1 | 80 | 36 | 15 | 1 |
| 25P | " | 1.6 | 1.8 | 1 | 90 | 43 | 14 | 0.4 |
| 25Q | D, 2CdG @ 50 ng/ml | 1.6 | 1.3 | 16 | 100 | 110 | 38 | 6 |
| 25R | " | 1.3 | 2.1 | 20 | 77 | 70 | 40 | 13 |
| 25S | L, 2-CdG @ 5 ug/ml | 1.5 | 2.0 | 97 | 50 | 67 | 77 | 90 |
| 25T | " | 0.9 | 1.1 | 86 | 88 | 110 | 120 | 120 |
| 25U | L, 2-CdG @ 500 ng/ml | 1.4 | 1.9 | 82 | 90 | 63 | 78 | 97 |
| 25V | " | 1.5 | 1.9 | 99 | 110 | 83 | 56 | 91 |
| 25W | L, 2-CdG @ 50 ng/ml | 1.3 | 1.4 | 90 | 48 | 47 | 90 | 90 |
| 25X | " | 0.8 | 1.1 | 76 | 67 | 83 | 63 | 61 |

@ Analysis of intracellular HBV DNA was 24 hours following the 10th day of treatment.

were used to correlate CPM measurements with relative levels of target HBV DNA. The levels of HBV DNA in each of three classes of intracellular viral genomic forms were individually quantitated: integrated HBV DNA, episomal monomeric genomes and HBV DNA replication intermediates (RI). Integrated HBV DNA was used to normalize the relative amounts of DNA in each lane because the levels of this class of HBV DNA would be expected to remain constant on a per cell basis. The levels of the monomeric HBV genomes and RI were used as an indicator of the relative level of HBV replication.

Levels of extracellular, or virion HBV DNA, in the culture medium and the levels of intracellular HBV DNA (Table 9), varied no more than 3-fold in the untreated control cell cultures. Ara-$\mu$MP and ddG were effective in reducing the levels of HBV DNA production and replication. The doses used were previously determined to be nontoxic (by measurement of cell growth rates) to 2.2.15.

The racemic (D,L) mixture of 2'-CdG was a potent inhibitor of HBV replication in 2.2.15 cells (Table 8). In comparison to ddG, 2'-CdG exhibited approximately the same level of inhibition of HBV replication at a 100-fold lower concentration. The minimal inhibitory concentration of approximately 50 ng/ml was approximately 10-fold higher than that originally reported for the racemic mixture on these same cells (Price et al., PNAS 86:806, 1989). The D isomer was as active an inhibitor of HBV replication as These data demonstrate that the D-isomer of 2'-CdG is considerably more potent against human CMV HSV-1 and HSV-2 in comparison to the D,L-mixture of 2'-CdG and is at least equally as potent as the racemic mixture against HBV, whereas the L-isomer demonstrated very little, if any, activity. However, we have also shown that, unexpectedly, D- and L-2'CdG are equally effective competitive inhibitors of the phosphorylation of thymidine by the virus-specific kinase, and do not differ in activity as substrates for the initial phosphorylation by the viral nucleoside kinase. Thus, while the difference in their effectiveness as antiviral agents appears to associated with the dramatic differences in the further phosphorylation of their monophosphates and in the polymerase-inhibitory activity of their triphosphates, it is apparent that the L-isomer is not totally inert in the cell. The total amount of L-2'CdG-monophosphate formed was greated than that of D-2'CdG-triphosphate. Although, it has been reported that very little if any short term cytotoxicity is associated with the L-isomer, long term effects L-2'CdG-monophosphate accumulation the host cells cannot be ruled out.

Thus, use of the purified D-isomer of 2'CdG as well as analogues and prodrugs of this compound in the treatment and prophylaxis of a number of viral infections provides the advantage of increased efficacy at a reduced dosage when compared to presently available agents and methods.

The composition can be administered at a dosage of between $10^{-5}$ and 10 mg/m$^2$/dose. The therapeutically antiviral effective amount of the compositions to be used in accordance with this invention to provide prophylaxis and treatment for individuals infected with, or at risk of being infected, can be optimized by methods known in the art. A preferred range is between $10^{-4}$ and $10^{-1}$ mg/m$^2$/dose. Dose frequency can be determined by measuring half-life according to standard techniques and preferably will be 1–3 times daily, although less frequent administration (every other day or even weekly) may have a positive effect. Treatment is continued until no further clinical improvement is observed (e.g., by viral load or other clinical measures), and preferably longer.

While we have hereinbefore presented a number of embodiments of this invention, it is apparent that our basic construction can be altered to provide other embodiments which utilize the processes of this invention. Therefore, it will be appreciated that the scope of this invention is to be defined by the claims appended hereto rather than the specific embodiments which are presented by way of example.

What is claimed is:

1. A method for preventing or treating a viral infection in a mammal characterized by administering an antiviral effective amount of a composition comprising a compound of the formula

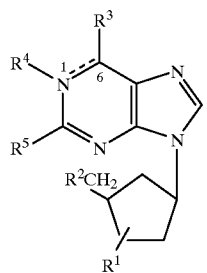

wherein, said composition comprises a substantial molar excess of the D-stereoisomer of said compound over the L-stereoisomer of said compound, $R^1$ is selected from the group consisting of, hydroxyl, and $C_1$–$C_6$ acyloxy;

$R^2$ is selected from the group consisting of hydroxyl, and $C_1$–$C_6$ acyloxy; and $R^3$ is oxygen bound through a double bond to carbon when $R^4$ is hydrogen, or $R^3$ is chosen from the group consisting of $C_1$–$C_6$ alkoxy, amino, and halogen when $R^4$ is bound to carbon 6 to form a double bond between the nitrogen of position 1 and the carbon of position 6 and $R^5$ is amino.

2. The method of claim 1 wherein said compound is 2'-CdG.

3. The method of claim 1 wherein said virus is a herpes virus.

4. The method of claim 3 wherein said virus is herpes simplex virus.

5. The method of claim 1 wherein said virus is cytomegalovirus.

6. The method of claim 1 wherein said virus is hepatitis B virus.

7. The method of claim 1 wherein said composition is administered orally.

8. The method of claim 1 wherein said composition comprises said compound in a pharmaceutically acceptable carrier.

* * * * *